(12) United States Patent
Kersey et al.

(10) Patent No.: US 8,541,172 B2
(45) Date of Patent: *Sep. 24, 2013

(54) METHOD FOR SEQUENCING A POLYNUCELOTIDE TEMPLATE

(75) Inventors: Alan D. Kersey, Wallingford, CT (US); Jonathan Mark Boutell, Walden (GB)

(73) Assignee: Illumina Cambridge Limited, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/445,072

(22) Filed: Apr. 12, 2012

(65) Prior Publication Data

US 2012/0258869 A1    Oct. 11, 2012

Related U.S. Application Data

(63) Continuation of application No. 12/559,902, filed on Sep. 15, 2009, now Pat. No. 8,182,994.

(51) Int. Cl.
*C12Q 1/68* (2006.01)
*C12P 19/34* (2006.01)
*G01N 33/48* (2006.01)

(52) U.S. Cl.
USPC ............................ 435/6.12; 435/91.2; 702/20

(58) Field of Classification Search
None
See application file for complete search history.

(56) References Cited

U.S. PATENT DOCUMENTS

| | | | |
|---|---|---|---|
| 5,302,509 A | 4/1994 | Cheeseman |
| 5,326,692 A | 7/1994 | Brinkley et al. |
| 5,405,746 A | 4/1995 | Uhlen |
| 5,432,065 A | 7/1995 | Fuller |
| 5,474,796 A | 12/1995 | Brennan |
| 5,508,169 A | 4/1996 | Deugau et al. |
| 5,514,539 A | 5/1996 | Bukh et al. |
| 5,547,839 A | 8/1996 | Dower et al. |
| 5,589,332 A | 12/1996 | Shih et al. |
| 5,616,478 A | 4/1997 | Chetverin |
| 5,629,158 A | 5/1997 | Uhlen |
| 5,641,658 A | 6/1997 | Adams et al. |
| 5,645,801 A | 7/1997 | Bouma et al. |
| 5,645,994 A | 7/1997 | Huang |
| 5,683,872 A | 11/1997 | Rudert et al. |
| 5,690,894 A | 11/1997 | Pinkel et al. |
| 5,753,439 A | 5/1998 | Smith et al. |
| 5,795,714 A | 8/1998 | Cantor et al. |
| 5,800,992 A | 9/1998 | Fodor et al. |
| 5,830,663 A | 11/1998 | Embleton et al. |
| 5,837,466 A | 11/1998 | Lane et al. |
| 5,843,660 A | 12/1998 | Schumm et al. |
| 5,922,574 A | 7/1999 | Minter |
| 5,928,875 A | 7/1999 | Breen et al. |
| 5,939,291 A | 8/1999 | Loewy et al. |
| 5,976,802 A | 11/1999 | Ansorge et al. |
| 6,060,288 A | 5/2000 | Adams et al. |
| 6,090,592 A | 7/2000 | Adams et al. |
| 6,107,023 A | 8/2000 | Reyes et al. |
| 6,280,949 B1 | 8/2001 | Lizardi |
| 6,316,229 B1 | 11/2001 | Lizardi et al. |
| 6,322,971 B1 | 11/2001 | Chetverin et al. |
| 6,326,489 B1 | 12/2001 | Church et al. |
| 6,406,893 B1 | 6/2002 | Knapp et al. |
| 6,432,680 B1 | 8/2002 | Lin et al. |
| 6,468,751 B1 | 10/2002 | Adams et al. |
| 6,489,103 B1 | 12/2002 | Griffiths et al. |
| 6,511,803 B1 | 1/2003 | Church et al. |
| 7,115,400 B1 | 10/2006 | Adessi et al. |
| 8,182,994 B2 * | 5/2012 | Kersey et al. ............... 435/6.12 |
| 2004/0096853 A1 | 5/2004 | Mayer |
| 2005/0100900 A1 | 5/2005 | Kawashima et al. |
| 2009/0088327 A1 | 4/2009 | Rigatti et al. |
| 2010/0111768 A1 | 5/2010 | Banerjee et al. |

FOREIGN PATENT DOCUMENTS

| | | |
|---|---|---|
| DE | 4141178 | 6/1993 |
| DE | 19515552 | 10/1996 |
| EP | 0 224 126 | 6/1987 |
| EP | 0 356 021 | 2/1990 |
| EP | 0 374 665 | 6/1990 |
| EP | 0 487 104 | 5/1992 |
| EP | 0 543 484 | 5/1993 |
| EP | 0 665 293 | 8/1995 |
| EP | 0 701 001 | 3/1996 |
| EP | 0 763 135 | 3/1997 |

(Continued)

OTHER PUBLICATIONS

Abel, "Fiber-Optic Evanescent Wave Biosensor for the Detection of Oligonucleotides", Analytical Chemistry, vol. 68:2905-2912 (1996).

(Continued)

*Primary Examiner* — Kenneth R. Horlick
*Assistant Examiner* — David Thomas
(74) *Attorney, Agent, or Firm* — Brent C. Moore; Illumina, Inc.

(57) ABSTRACT

Improved compositions, methods, apparatus, and kits for high-throughput nucleic acid amplification, detection and sequencing are disclosed. A nucleic acid cluster having an identifiable center is produced by generating on a solid support an immobilized nucleic acid complement from a template, one of which comprises a detectable label; and amplifying the complement and the template to obtain a nucleic acid cluster on the support, the cluster having a substantially central location marked by the detectable label and a surrounding region comprising immobilized copies. Also disclosed are nucleotide sequence determination in nucleic acid clusters so produced, center position annotation in the clusters, assignment of sequence information to overlapping clusters, and related compositions and methods.

26 Claims, 3 Drawing Sheets

(56) References Cited

FOREIGN PATENT DOCUMENTS

| | | |
|---|---|---|
| EP | 1 019 496 | 7/2000 |
| EP | 1 482 036 | 12/2004 |
| EP | 1 117 827 | 11/2005 |
| GB | 2233654 | 1/1991 |
| WO | WO 87/06270 | 10/1987 |
| WO | WO 88/10315 | 12/1988 |
| WO | WO 89/01050 | 2/1989 |
| WO | WO 89/09282 | 10/1989 |
| WO | WO 90/02205 | 3/1990 |
| WO | WO 90/06042 | 6/1990 |
| WO | WO 90/09455 | 8/1990 |
| WO | WO 90/11369 | 10/1990 |
| WO | WO-9106678 | 5/1991 |
| WO | WO 92/04469 | 3/1992 |
| WO | WO 92/10587 | 6/1992 |
| WO | WO 93/03151 | 2/1993 |
| WO | WO 93/04199 | 3/1993 |
| WO | WO 93/09250 | 5/1993 |
| WO | WO 93/21340 | 10/1993 |
| WO | WO 94/02634 | 2/1994 |
| WO | WO 94/05414 | 3/1994 |
| WO | WO 94/24312 | 10/1994 |
| WO | WO 95/12416 | 5/1995 |
| WO | WO 95/33073 | 12/1995 |
| WO | WO 96/04404 | 2/1996 |
| WO | WO 96/24688 | 8/1996 |
| WO | WO 96/27025 | 9/1996 |
| WO | WO 96/32504 | 10/1996 |
| WO | WO 96/34114 | 10/1996 |
| WO | WO 96/36737 | 11/1996 |
| WO | WO 97/19193 | 5/1997 |
| WO | WO 97/41256 | 11/1997 |
| WO | WO 97/45554 | 12/1997 |
| WO | WO 98/36094 | 8/1998 |
| WO | WO 98/44151 | 10/1998 |
| WO | WO 98/44152 | 10/1998 |
| WO | WO 98/45474 | 10/1998 |
| WO | WO 00/41524 | 7/2000 |
| WO | WO 00/75374 | 12/2000 |

OTHER PUBLICATIONS

Babic et al., "MutS interaction with mismatch and alkylated base containing DNA molecules detected by optical biosensor", Mutation Research 372:87-96 (1996).

Beattie et al., "Hybridization of DNA targets to glass-tethered oligonucleotide probes", Molecular Biotechnology, 4:213-225 (1995).

Blanchard et al., "Oligonucelotide array synthesis using ink jets", Genome Science and Technology 1(3):225 (1996).

Bronk et al., "Combined imaging and chemical sensing using a single optical imaging fiber", Anal. Chem. 67:2750-2757 (1995).

Chee et al., "Accessing genetic information with high-density DNA arrays", Science 274:601 (2001).

Chen et al., "Isolation of Plasmid DNA Rescued From Single Colonies of Agrobacterium Tumefaciens by Means of Rolling Circle Amplification", Plant Molecular Biology Reporter, 21:411-415 (2003).

Cheng et al., "Chip PCR II Investigation of different PCR amplification systems in microfabricated silicon-glass chips", Nucleic Acids Research 24:380-385 (1996).

Chrisey et al., "Covalent attachment of synthetic DNA to self-assembled monolayer films", NAR, 24(15):3031-3039 (1996).

Chu et al., "Derivitization of unprotected polynucleotides", NAR, 11 (18):6514-6529 (1983).

Drmanac et al., "Sequencing by hybridization: towards an automated sequencing of one million m13 clones arrayed on membranes", Electrophoresis 13:566-573 (1992).

Egan et al., "Structural studies and chemistry of bacterial polysaccharides. Investigations of Phosphodiester-Linked Capsular Polysaccharides Isolated from Haemophilus influenzae Types a, b, c, and f: NMR Spectroscopic Identification and Chemical Modification of End", Groups and the Nture of Base-Catalyzed Hydrolytic Depolymerization, J. Am. Chem. Soc., 104:2898-2910 (1982).

Eggleston et al., "A helicase assay based on the displacement of fluorescent nucleic acid-binding ligands", Nucleic Acids Research 24(7):1179-1186 (1996).

Ferguson et al., "A Fiber-Optic DNA Biosensor Microarray for the Analysis of Gene Expression", Nature Biotechnol. vol. 14:1681-1684 (1996).

Fodor, "Light-Directed, Spatially Addressable Parallel Chemical Synthesis", Science, vol. 251:767-773 (1991).

Fu et al., "Sequencing Double-stranded DNA by Strand Displacement", Nucleic Acids Research vol. 25 No. 3:677-679 (1997).

Ghosh et al., "Covalent attachment of oligonucleotides to solid supports", NAR, 15(13):5353-5371 (1987).

Gilham, "The synthesis of Celluloses covalently bound nucleotides, polynucleotides, and nucleic acids", Biochemistry, 2810-2813 (1968).

Gingeras et al., "Hybridization properties of immobilized nucleic acids", NAR, 15:5373-5390 (1987).

Guo et al., "Direct fluorescence analysis of genetic polymorphisms by hybridization with oligonucleotide arrays on glass supports", Nucleic Acids Research, vol. 22(24):5456-5465 (1994).

Hahn et al., "Quantitative polymerase chain reaction with enzyme-linked immunosorbent assay detection of selectively digested amplified sample and control DNA", Anal Biochem 229:236-248 (1995).

Higuchi et al., "Kinetic PCR analysis: real-time monitoring of DNA amplification reactions", Bio/Technology 11:1026-1030 (1993).

Joos et al., "Covalent attachment of hybridizable oligonucleotides to glass supports", Analytical Biochemistry, 247:96-101 (1997).

Kaneoka et al., "Solid-phase direct DNA sequencing of allele specific polymerase chain reaction amplified HLA-DR genes", Biotechniques 10(1):30, 32, 34 (1991).

Kremsky et al., "Immobilization of DNA oligonucelotides containing an aldehyde or carboxylic acid group at the 5' terminus", NAR 15 (7):2891-2909 (1987).

Kulp et al., "Polymer immobilized enzyme optrodes for the detection of penicillin", Anal. Chem. 59:2849-2853 (1987).

Lambert et al., "cDNA library construction from small amounts of RNA using paramagnetic beads and PCR", Nucleic Acids Research 21(3):775-6 (1993).

Lamture et al., "Direct Detection of Nucleic Acid Hybridization on the Surface of a Charge Coupled-Device", Nucleic Acids Research, 22(11): 2121-2125 (1994).

Lizardi, "Mutation detection and single-molecule counting using isothermal rolling-circle amplification", Nature Genetics, vol. 19:225-232 (1998).

Lockhart et al., "Expression monitoring by hybridization to high-density oligonucleotide arrays", Nature Biotechnology, 14:1675-1680 (1996).

Ludecke et al., "Cloning defined regions of the human genome by microdissection of banded chromosomes and enzymatic amplification", Nature 338:348-350 (1989).

Lund et al., "Assessment of methods for covalent binding of nucleic acids to magnetic beads, Dynabeads, and the characteristics of the bound nucleic acids in hybridization reactions", NAR, 16 (22):10860-10881 (1988).

Manley et al., "DNA-dependent transcription of adenovirus genes in a soluble whole-cell extract", PNAS 77(7):3855-3859 (1980).

Maskos et al., "Oligonucleotide Synthesis and Hybridisations on Glass Supports: a Novel Linker for Oligonucleotide Synthesis and Hybridisation Properties of Oligonucleotides Synthesized in Situ", Nucleic Acids Researc, 20(7):1679-1684 (1992).

Maskos et al., "Parallel analysis of oligodeoxyribonucleotide (oligonucleotide) interaction. I. Analysis of factors influencing oligonucleotide duplex formation", Nucleic Acids Research 20(7):1675-1678 (1992).

Munkholm et al., "Polymer modification of fiber optical imaging fibers", Analytical Chemistry 58(7):1427-1430 (1986).

Notomi et al., "Loop-mediated isothermal amplification of DNA", Nucleic Acids Research 28:i-vii (2000).

Ochman et al., "Genetic applications of an Inverse Polymerase Chain Reaction", Genetics 120:621-623 (1988).

O'Donnell-Maloney et al., "The development of microfabricated array for DNA sequencing and analysis", Tibtech, 14:401-407 (1996).

Oroskar et al., "Detection of immobilized amplicons by ELISA-like techniques", Clinical Chemistry 42:1547-1555 (1996).

Pease et al., "Light-generated oligonucleotide array for rapid DNA sequence analysis", Proc. Natl. Acad. Sci., 91(11):5502-5026 (1994).

Peeters et al., "Comparison of four biofuncitonal reagents for coupling peptides to proteins and the effect of the three moities on the immunogenicity of the conjugates", Journal of Immunological Methods 120:133-143 (1989).

Pirrung et al., "Comparison of Methods for Photochemical Phosphoramidite-Based DNA Synthesis", Journal of Organic Chemistry 60(20):6270-6276 (1995).

Piunno et al., "Fiber-optic DNA sensor for fluorometric nucleic acid determination", Anal. Chem. 67:2635-2643 (1995).

Rasmussen et al., "Covalent immobilization of DNA onto polystyrene microwells: The molecules are only bound at the 5' end", Analytical Biochemistry, 198:138-142 (1991).

Saiki et al., "Enzymatic amplification of B-globin genomic sequences and restriction site analysis for diagnosis of sicke cell anemia", Science 230:1350-1354 (1985).

Saiki et al., "Genetic analysis of amplified DNA with immobilized sequence-specific oligonucleotide probes", PNAS 86:6230-4 (1989).

Saunders et al., "PCR amplification of DNA microdissected from a single polytene chromosome band: a comparison with conventional microcloning", Nucleic Acids Research 17:9027-9037 (1989).

Stamm et al., "Sanchored PCR: PCR with cDNA couples to a solid phase", Nucleic Acids Research 19(6):1350 (1991).

Steigerwald et al., "Ligation-mediated PCR Improves the sensitivity of methylation analysis by restriction enzymes and detection of specific DNA Strand breaks", Nucleic Acids Research 18:1435-1439 (1990).

Sterky et al., "Direct sequencing of bacterial artificial chromosomes [bacS] prokaryotic genomes by biotin capture PCR", Journal of Biotechnology, vol. 60:119-129 (1998).

Thomas et al., "Affymetrix: Genes on Chips", Expr. Opino. Ther. Patents 8:503-508 (1998).

Triglia et al., "A procedure for in vitro amplification of DNA segments that lie outside the boundaries of know sequences", Nucleic Acids Research 16:8186 (1988).

Vanness et al., "A versatile solid support system for oligodeoxynucleotide probe-based hybridization assays", Nucleic Acids Research 19(12):3345-3350 (1991).

Vos et al., "AFLP: a new technique for DNA Fingerprinting", NAR 23(21):4407-4414 (1995).

Walker, "Empirical Aspects of Strand Displacement Amplification", PCR Methods Appl 3:1-6 (1993).

Walker et al., "Isothermal in vitro amplification of DNA by a restriction enzyme/DNA polymerase system", PNAS, 89:392-396 (1992).

Walker et al., "Multiplex strand displacement amplification (SDA) and detection of DNA sequences from Mycobacterium tuberculosis and other mycobacteria", Nucleic Acids Research 22:2670-2677 (1994).

Westin et al., "Anchored multiplex amplification on a microelectric chip array", Nature Biotechnology 18:199-204 (2000).

Winn-Deen et al., "Non-radioactive detection of mycobacterium tuberculosis LCR products in a microtiter plate format", Mol. Cell. Probes 7:179-186 (1993).

Wolf et al., "Rapid hybridization kinetics of DNA attached to submicron latex particles", NAR, 15:2911-2926 (1987).

Yang et al., "Covalent Immobilization of oligonucleotides on modified glass/silicon surfaces for solid-phase DNA hybridization and amplification", Chemistry Letters, 257-8 (1988).

Yershov et al., "DNA analysis and diagnostics on oligonucleotide microchips", PNAS US 93:4913-4918 (1996).

* cited by examiner

METHOD FOR SEQUENCING A POLYNUCELOTIDE TEMPLATE

CROSS REFERENCE TO RELATED APPLICATIONS

The present application is a continuation of U.S. Ser. No. 12/559,902, filed Sep. 15, 2009. The entire disclosure of which is incorporated herein by reference in its entirety.

BACKGROUND

1. Technical Field

The present invention generally relates to the field of nucleic acid amplification, detection and sequencing. More specifically, the present invention relates to improved compositions, methods, apparatus, and kits for high-throughput nucleic acid amplification, detection and sequencing.

2. Description of the Related Art

High-throughput technologies have become a cornerstone in many areas of modern molecular biology, biotechnology and medicine. For example, efforts to rapidly, accurately, and economically determine gene expression levels (e.g., microarrays) and nucleic acid sequence (e.g., parallel sequencing) have intensified over the past few years. The information provided by such advances has furthered genome analyses for several plant and animal species, including humans, non-human primates and others, and has also assisted drug target discovery and validation, disease diagnosis and risk scoring, and the identification and characterization of multiple organisms.

A number of methods of nucleic acid sequencing are well known and documented in the art. The two most commonly used methods are the Maxam and Gilbert technique and the widely used Sanger sequencing technique.

In Sanger sequencing, each nucleic acid molecule to be sequenced is used as a template that is replicated in a reaction employing DNA polymerase as a catalytic enzyme, and deoxynucleotide triphosphates (dNTPs) ATP, CTP, GTP and TTP as precursors to be incorporated into a DNA complement of the template and dideoxynucleotide triphosphates of adenine (A), guanine (G), cytosine (C) and thymidine (T) (ddNTPs) as chain terminators. The DNA polymerase can incorporate both dNTPs and ddNTPs into the growing DNA strand. The incorporation of a ddNTP, however, terminates the nucleic acid chain extension because the ddNTP lacks a 3' hydroxyl group and thus is no longer a substrate for further chain elongation. For example, in a particular template-directed Sanger sequencing reaction in which only one type of ddNTP (e.g., ddCTP) is present, a mixture of nucleic acids of different lengths is produced, all terminating with the same ddNTP (e.g., ddCTP). Typically, either separate reactions are set up for each of the four types of ddNTPs or the four ddNTPs are differentially labeled and used in a single reaction, and size distribution of the nucleic acid fragment products is analyzed by denaturing gel electrophoresis or by mass spectrometry. For example, each of the ddNTPs in the reaction mixture is labeled with a different fluorophore to enable detection of the fragments of different lengths.

The above described methods are disadvantageous because each nucleic acid to be sequenced has to be processed individually during the sequencing reaction. Gel electrophoresis is not well suited for large scale high throughput sequencing. It is cumbersome, labor intensive, and intrinsically slow, even when capillary gel electrophoresis is used. In addition, following electrophoretic separation of reaction products, the subsequent analysis of electrophoretograms for determination of the sequence is time-consuming and can generate equivocal results due to confounding artifacts. Mass spectrometry offers more promise for expediting sequence determination, but it is still at the prototype level, requires very expensive apparatus and labor-intensive instrument maintenance, and each sample must be analyzed individually.

More recently, nucleic acid sequencing methods based on solid-phase DNA chips and DNA hybridization have become available. Each of these methods is not without its shortcomings, however, because DNA chips have to be carefully designed, fastidiously manufactured, and subjected to rigorous quality control testing. These processes are lengthy and require significant expertise, which drives up the price of individual chips. Moreover, often the chips are not reusable and thus for each chip, only one nucleic acid sample (e.g., one patient to be diagnosed) can be processed at a time.

In many currently practiced techniques for nucleic acid sequence analysis, amplification of the nucleic acids of interest is a prerequisite step in order to obtain the nucleic acid in a quantity sufficient for analysis. Several methods of nucleic acid amplification are well known and documented in the art. For example, nucleic acids can be amplified by inserting a nucleic acid of interest into an expression vector construct. Such vectors can then be introduced into suitable biological host cells and the vector DNA, including the nucleic acid of interest, is amplified by culturing the biological host using well established protocols. However, such methods have the disadvantage of being time consuming, labor intensive, and difficult to automate.

The technique of DNA amplification by the polymerase chain reaction (PCR) is a widely used and well documented method. In PCR, a target nucleic acid fragment of interest can be amplified using one or two short oligonucleotide sequences (usually referred to as primers) that specifically hybridize (e.g., by Watson-Crick base-pairing) to known sequences flanking the DNA sequence that is to be amplified. By repeated cycles of heat denaturation, primer hybridization, and extension, the target nucleic acid is exponentially amplified. Traditionally, this method is performed in solution and the amplified target nucleic acid fragment is purified from solution by methods well known in the art, for example, by gel electrophoresis.

More recently, nucleic acid amplification methods have been disclosed which employ an immobilized primer grafted to a solid-phase surface in conjunction with free primers in solution. These methods allow the simultaneous amplification and attachment of a PCR product onto the surface.

Some known methods of nucleic acid analysis involve PCR-based amplification of a target nucleic acid only when the target nucleic acid is present in the sample being tested. For the amplification of the target sequence, primers can be attached to a solid support, which results in the amplified target nucleic acid sequences also being attached to the solid support. This amplification technique is often referred to as the "bridge amplification" technique. In this technique, conventional PCR primers can be designed to hybridize specifically to polynucleotide sequences flanking the particular target nucleic acid sequence to be amplified. If the target nucleic acid is present in the sample, it hybridizes to the primers and is amplified by PCR. The first step in this PCR amplification process is thus the hybridization of the target nucleic acid to a first specific primer attached to the support ("primer 1"). A first amplification product, which is complementary to the target nucleic acid, is then formed by extension of the primer 1 sequence. Denaturation conditions release the target nucleic acid, which can then either participate in further hybridization reactions with other primer 1 sequences attached to the support or be removed from the solid support. The first amplification product, which is attached to the support, can then hybridize with a second specific primer ("primer 2") attached to the support and a second amplification product comprising an attached nucleic acid sequence complementary to the first amplification product can be formed by extension of the primer 2 sequence. Thus, the target nucleic acid and the first and second amplification products are capable of participating in a plurality of hybridization and extension reactions, which are limited by the initial presence or absence of the target nucleic acid and by the number of primer 1 and primer 2 sequences initially attached to the solid support.

A bridge amplification technique can be used to amplify several different target nucleic acid sequences simultaneously by arraying different sets of first and second primers, each set being specific for a different target nucleic acid sequence, on different or overlapping regions of the solid support. A further application of the bridge amplification technique is to amplify fragments using immobilized primers which are complementary to a universal sequence located at the ends of a collection of templates of different sequence. Thus the primer 1 and primer 2 sequences may be complementary to a nucleic acid sample with known ends, for example, ends that have been attached to the sample by ligation of a universal adapter sequence. The templates may be applied to the solid support as single strands where the ends of each strand are complementary to, and hybridize with, the primer 1 and/or primer 2 sequences. Primer 1 can be extended to form an extension product where the end of the extension product is complementary to the primer 2 sequence. Likewise, primer 2 can be extended to form an extension product where the end of the extension product is complementary to the primer 1 sequence. The hybridized targets can be denatured and removed from the support. The first extension products can be hybridized with the primer 1 and primer 2 sequences and extended to form second extension products wherein the second extension products are complementary copies of the first extension products. The first and second extension products can be amplified via cycles of denaturation, hybridization and extension to produce multiple copies of each of the first and second extension products. The amplification may give rise to a population of nucleic acid clusters attached to the support where each cluster is derived from a single template, but adjacent clusters on the solid support contain different template sequences.

In the era of high-throughput technology, amassing the highest yield of interpretable data at the lowest cost per effort remains a significant challenge. Cluster-based methods of nucleic acid sequencing, such as those that utilize bridge amplification for cluster formation, have made a valuable contribution toward the goal of increasing the throughput of nucleic acid sequencing. These cluster-based methods rely on sequencing a dense population of nucleic acids immobilized on a solid support, and typically involve the use of image analysis software to deconvolute optical signals generated in the course of simultaneously sequencing multiple clusters situated at distinct locations on a solid support.

However, such solid-phase nucleic acid cluster-based sequencing technologies still face considerable obstacles that limit the amount of throughput that can be achieved. For example, in cluster-based sequencing methods, determining the nucleic acid sequences of two or more clusters that are physically too close to one another to be resolved spatially, or that in fact physically overlap on the solid support, can pose an obstacle. For example, current image analysis software can require valuable time and computational resources for determining from which of two overlapping clusters an optical signal has emanated. As a consequence, compromises are inevitable for a variety of detection platforms with respect to the quantity and/or quality of nucleic acid sequence information that can be obtained.

High density nucleic acid cluster-based genomics methods extend to other areas of genome analysis as well. For example, nucleic acid cluster-based genomics can be used in sequencing applications, diagnostics and screening, gene expression analysis, epigenetic analysis, genetic analysis of polymorphisms, and the like. Each of these nucleic acid cluster-based genomics technologies, too, is limited when there is an inability to resolve data generated from closely proximate or spatially overlapping nucleic acid clusters.

Clearly there remains a need for increasing the quality and quantity of nucleic acid sequencing data that can be obtained rapidly and cost-effectively for a wide variety of uses, including for genomics (e.g., for genome characterization of any and all animal, plant, microbial or other biological species or populations), pharmacogenomics, transcriptomics, diagnostics, prognostics, biomedical risk assessment, clinical and research genetics, personalized medicine, drug efficacy and drug interactions assessments, veterinary medicine, agriculture, evolutionary and biodiversity studies, aquaculture, forestry, oceanography, ecological and environmental management, and other purposes. The presently disclosed invention embodiments provide compositions and methods that address these and similar needs, including compositions and methods to increase the level of throughput in high-throughput nucleic acid sequencing technologies, and offer other related advantages. These and other aspects of the present invention will become apparent upon reference to the following detailed description.

BRIEF SUMMARY

According to certain embodiments of the present invention there is provided a method for producing at least one nucleic acid cluster having an identifiable center, comprising (I) generating, on a solid support, at least one immobilized nucleic acid complement of at least one nucleic acid template, wherein the at least one nucleic acid template or the at least one nucleic acid complement comprises a detectable label; and (II) amplifying the at least one nucleic acid template and the at least one nucleic acid complement to obtain on the solid support at least one nucleic acid cluster, wherein each cluster comprises (a) a substantially central location comprising the at least one nucleic acid template and the at least one nucleic acid complement, and (b) a surrounding region comprising one or more immobilized copies of the at least one nucleic acid template and of the at least one nucleic acid complement, and thereby producing the at least one nucleic acid cluster having an identifiable center.

In certain further embodiments the one or more immobilized copies of the at least one nucleic acid template and the at least one nucleic acid complement at the surrounding region lack the detectable label, and whereby the detectable label distinguishes the substantially central location from the surrounding region. In certain embodiments at least 100 nucleic acid clusters each having an identifiable center are produced per square centimeter on the solid support. In certain embodiments the step of amplifying is repeated one or a plurality of times under conditions and for a time sufficient for the detectable label to remain at the substantially central location in the at least one nucleic acid cluster. In certain embodiments the at least one nucleic acid template is immobilized via its 5' end to the solid support. In certain embodiments step (I) comprises generating at least one immobilized detectably labeled central nucleic acid complement of the at least one nucleic acid template, on the solid support, wherein the solid support comprises one or more immobilized oligonucleotide primers X, and wherein (a) the at least one nucleic acid template has a 5' end and a 3' end and comprises an oligonucleotide sequence Y at the 5' end and an oligonucleotide sequence Z at the 3' end, (b) each of the one or more immobilized oligonucleotide primers X (i) is immobilized at its 5' end to the solid support and (ii) is capable of hybridizing to the oligonucleotide sequence Z, and (c) the at least one immobilized detectably labeled central nucleic acid complement comprises (i) an extension of one of the immobilized oligonucleotide primers X, and (ii) at least one detectable label. In certain further embodiments the oligonucleotide sequence Z is complementary to the oligonucleotide sequence Y and the immobilized oligonucleotide primer X comprises a sequence that is substantially identical to oligonucleotide sequence Y. In certain other further embodiments the solid support comprises a first and a second immobilized oligonucleotide primer X which are different from each other, wherein the oligonucleotide sequence Z can hybridize to the first immobilized oligonucleotide primer X and the second immobilized oligonucleotide primer X has a sequence that is substantially identical to oligonucleotide sequence Y. In certain other further embodiments generating comprises (a) initiating, in the presence of one or more labeled nucleotides that each comprise a detectable label, a primer extension reaction on the at least one nucleic acid template whereby the one or more immobilized oligonucleotide primers X are extended by incorporation, into the immobilized detectably labeled central nucleic acid complement, of one or more of said labeled nucleotides that each comprise a detectable label; (b) stopping the primer extension reaction and removing therefrom unincorporated labeled nucleotides; and (c) re-initiating the primer extension reaction in the presence of unlabeled nucleotides. In certain further embodiments steps (a) and (b) are repeated one or a plurality of times, wherein a single nucleotide comprising a detectable label is incorporated into the central nucleic acid complement at each step (a).

According to certain of the herein described embodiments, amplifying comprises thermocycling amplification, and in certain embodiments amplifying comprises isothermal amplification.

According to certain embodiments the herein described method further comprises recording a center position in the nucleic acid cluster by detecting the at least one detectable label and therefrom identifying the substantially central location in the cluster. In certain further embodiments the method comprises determining a nucleotide sequence in the at least one nucleic acid cluster by performing one or a plurality of sequencing steps on at least one of (i) the at least one nucleic acid template or an immobilized copy thereof, and (ii) the immobilized detectably labeled central nucleic acid complement or an immobilized copy thereof. In a further embodiment each sequencing step comprises incorporating a labeled sequencing nucleotide into the at least one nucleic acid cluster; and subsequently detecting the incorporated labeled sequencing nucleotide in the at least one nucleic acid cluster. In certain other further embodiments, full or partial nucleotide sequences are determined simultaneously in more than one nucleic acid cluster, each of the more than one clusters having an identified substantially central location. According to certain related embodiments, (i) full or partial nucleotide sequences are determined simultaneously in more than one nucleic acid cluster, each of said more than one clusters having an identifiable center, (ii) each sequencing step further comprises detecting a position of the incorporated labeled sequencing nucleotide on the solid support, and (iii) a determined sequence can be assigned to a discrete nucleic acid cluster when there is a substantial correlation between (i) the recorded center position of each nucleic acid cluster and (ii) the position of each incorporated labeled sequencing nucleotide on the solid support that is detected in each sequencing step. In certain further embodiments, for each of two or more overlapping nucleic acid clusters, the determined nucleotide sequence is assigned to one discrete nucleic acid cluster.

According to certain embodiments of the above described methods, the step of recording is performed prior to amplifying of step (II), and in certain other embodiments the step of recording is performed after amplifying of step (II). In certain other embodiments the one or more detectable labels are not detectably discrete from any incorporated labeled sequencing nucleotide detected at each sequencing step. In certain embodiments the step of recording is performed at each sequencing step. In certain embodiments the one or more detectable labels are detectably discrete from each of the incorporated labeled sequencing nucleotides detected at each sequencing step.

In certain other embodiments of the present invention there is provided a method for annotating a center position of at least one nucleic acid cluster, comprising: (I) generating, on a solid support, at least one immobilized nucleic acid complement of at least one nucleic acid template, wherein the at least one nucleic acid template or the at least one nucleic acid complement comprises a detectable center label; and (II) amplifying the at least one nucleic acid template and the at least one nucleic acid complement to obtain on the solid support at least one nucleic acid cluster, wherein each cluster comprises (a) a substantially central location comprising the at least one nucleic acid template and the at least one nucleic acid complement, and (b) a surrounding region comprising one or more immobilized copies of the at least one nucleic acid template and of the at least one nucleic acid complement; and (III) recording a center position in the at least one nucleic acid cluster by detecting the detectable center label to identify the substantially central location in the at least one nucleic acid cluster as the center position, and thereby annotating the center position of the at least one nucleic acid cluster.

In certain further embodiments the one or more immobilized copies of the at least one nucleic acid template and the at least one nucleic acid complement at the surrounding region lack the detectable center label, and whereby the detectable center label distinguishes the substantially central location from the surrounding region. In another embodiment at least 100 nucleic acid clusters each having an annotated center position are produced per square centimeter on the solid support. In another embodiment the step of amplifying is repeated one or a plurality of times under conditions and for a time sufficient for the detectable center label to remain at the substantially central location in the at least one nucleic acid cluster. In another embodiment the at least one nucleic acid template is immobilized via its 5' end to the solid support. In another embodiment step (I) comprises generating at least one immobilized detectably labeled central nucleic acid complement of the at least one nucleic acid template, on the solid support, wherein the solid support comprises one or more immobilized oligonucleotide primers X, and wherein (a) the at least one nucleic acid template has a 5' end and a 3' end and comprises an oligonucleotide sequence Y at the 5' end and an oligonucleotide sequence Z at the 3' end, (b) each of the one or more immobilized oligonucleotide primers X (i) is immobilized at its 5' end to the solid support and (ii) is capable of hybridizing to the oligonucleotide sequence Z, and (c) the at least one immobilized detectably labeled central nucleic acid complement comprises (i) an extension of one of the immobilized oligonucleotide primers X, and (ii) at least one detectable label. In certain further embodiments the oligonucleotide sequence Z is complementary to the oligonucleotide sequence Y and the immobilized oligonucleotide primer X comprises a sequence that is substantially identical to oligonucleotide sequence Y. In certain other further embodiments the solid support comprises a first and a second immobilized oligonucleotide primer X which are different from each other, wherein the oligonucleotide sequence Z can hybridize to the first immobilized oligonucleotide primer X and the second immobilized oligonucleotide primer X has a sequence that is substantially identical to oligonucleotide sequence Y. In certain other further embodiments, the step of generating comprises (a) initiating, in the presence of one or more labeled nucleotides that each comprise a detectable center label, a primer extension reaction on the at least one nucleic acid template whereby the one or more immobilized oligonucleotide primers X are extended by incorporation, into the at least one immobilized detectably labeled central nucleic acid complement, of one or more of said labeled nucleotides that each comprise a detectable center label; (b) stopping the primer extension reaction and removing therefrom unincorporated labeled nucleotides; and (c) re-initiating the primer extension reaction in the presence of unlabeled nucleotides. In certain embodiments steps (a) and (b) are repeated one or a plurality of times, and wherein a single nucleotide comprising a detectable center label is incorporated into the at least one central nucleic acid complement at each step (a).

In certain other further embodiments there is provided a method comprising determining a nucleotide sequence in the at least one nucleic acid cluster by performing one or a plurality of sequencing steps on at least one of (i) the at least one nucleic acid template or an immobilized copy thereof, and (ii) the at least one immobilized detectably labeled central nucleic acid complement or an immobilized copy thereof. In a further embodiment each sequencing step comprises incorporating a labeled sequencing nucleotide into the at least one nucleic acid cluster; and subsequently detecting said incorporated labeled sequencing nucleotide in the at least one nucleic acid cluster. In another further embodiment full or partial nucleotide sequences are determined simultaneously in more than one nucleic acid cluster, each having an identified center position. In certain related embodiments, (i) full or partial nucleotide sequences are determined simultaneously in more than one nucleic acid cluster, each having an identified center position, (ii) each sequencing step further comprises detecting a labeled sequencing nucleotide position of the incorporated labeled sequencing nucleotide on the solid support, and (iii) a determined sequence can be assigned to a discrete nucleic acid cluster when there is a substantial correlation between (i) the recorded center position of each of the more than one nucleic acid clusters and (ii) the labeled sequencing nucleotide position of each incorporated labeled sequencing nucleotide on the solid support that is detected in each sequencing step. In certain embodiments, for each of two or more overlapping nucleic acid clusters, the determined nucleotide sequence is assigned to one discrete nucleic acid cluster.

In certain embodiments of the herein described methods, the step of recording is performed prior to amplifying of step (II), and in certain embodiments the step of recording is performed after amplifying of step (II). In certain embodiments the at least one detectable center label is not detectably discrete from any incorporated labeled sequencing nucleotide that is detected at each sequencing step. In certain embodiments the step of recording is performed at each sequencing step. In certain embodiments the step of recording is performed at each sequencing step and the at least one detectable center label is detectably discrete from each of the incorporated labeled sequencing nucleotides detected at each sequencing step. In certain embodiments the step of amplifying is selected from a step that comprises thermocycling amplification and a step that comprises isothermal amplification.

In certain embodiments of the present invention there is provided a method for assigning nucleotide sequence information to at least one of two or more nucleic acid clusters that overlap on a solid support, comprising (a) providing two or more nucleic acid clusters that detectably overlap on a solid support, each of said clusters comprising (i) a substantially central location comprising an immobilized central nucleic acid having a detectable center label, and (ii) a surrounding region comprising one or more immobilized copies of the immobilized central nucleic acid, wherein the detectable center label distinguishes the substantially central location from the surrounding region; (b) detecting the detectable center label in each of said overlapping nucleic acid clusters and therefrom identifying in each cluster a first position for the substantially central location on the solid support; (c) determining a nucleotide sequence in at least one cluster of said overlapping nucleic acid clusters by performing one or a plurality of sequencing steps thereupon, thereby identifying a second position for the at least one cluster on the solid support; and (d) assigning a nucleotide sequence determined in (c) to a discrete nucleic acid cluster by substantially correlating (i) the first position for the substantially central location of (b) with (ii) the second position for the at least one cluster on the solid support of (c), and thereby assigning nucleotide sequence information to at least one of two or more nucleic acid clusters that overlap on the solid support.

In certain further embodiments each sequencing step comprises (i) incorporating one or more detectably labeled sequencing nucleotides into the nucleic acid cluster, and (ii) detecting a second position on the solid support for each of the one or more incorporated detectably labeled sequencing nucleotides. In certain other further embodiments, two, three, four, five, or six overlapping nucleic acid clusters are each assigned to a discrete nucleic acid cluster. In certain other further embodiments, each detectable center label is not detectably discrete from any incorporated labeled sequencing nucleotide detected at each sequencing step. In certain other embodiments the step of recording is performed for each sequencing step. In certain further embodiments, each detectable center label is detectably discrete from any incorporated labeled sequencing nucleotide detected at each sequencing step.

In other embodiments there is provided by the present invention a composition comprising (a) a solid support; and (b) one or more nucleic acid clusters each comprising a plurality of nucleic acids having the same sequence and being immobilized to the solid support, wherein each nucleic acid cluster comprises an identifiable center comprising a first subpopulation of the plurality of nucleic acids that is surrounded by a second subpopulation of the nucleic acids, wherein each of the nucleic acids in the first subpopulation comprises one or more detectable center labels that distinguish the nucleic acids in the first subpopulation from the nucleic acids in the second population. In certain embodiments the composition comprises one or more oligonucleotide primers X. In certain embodiments the nucleic acids of (i) and (ii) are single stranded. In certain embodiments the nucleic acid clusters are covalently immobilized to the solid support by a chemically modifiable functional group. In certain further embodiments the chemically modifiable functional group is selected from a phosphate group, a carboxylic moiety, an aldehyde moiety, a thiol, a hydroxyl, a dimethoxytrityl (DMT) and an amino group. In certain embodiments the chemically modifiable functional group comprises an amino group. In certain embodiments of the herein described composition, the solid support to which the 5' ends are immobilized comprises a support that is selected from optical fibers, latex beads, dextran beads, polystyrene, polypropylene, a polyacrylamide gel, gold surfaces, glass surfaces and silicon wafers. In certain embodiments the solid support is glass. In certain embodiments of the herein described composition, the density of each of the one or more nucleic acid clusters on the solid support is $10,000/mm^2$ to $100,000/mm^2$. In certain embodiments of the herein described composition, the diameter of each of the one or more nucleic acid clusters is about 0.2 micrometers to about 6 micrometers. In certain embodiments of the herein described composition, the diameter of each of the one or more nucleic acid clusters is about 0.5 micrometers to about 3 micrometers. In certain embodiments of the herein described composition, at most 50 percent of the copies of the detectably labeled central nucleic acid complement comprise one or more detectable center labels. In certain embodiments of the herein described composition, at most 5 percent of the copies of the detectably labeled central nucleic acid complement comprise one detectable center label. In certain embodiments of the herein described composition, each nucleic acid cluster comprises one detectably labeled central nucleic acid complement. In certain further embodiments the detectably labeled central nucleic acid complement comprises one or more detectable center labels. In certain still further embodiments the detectably labeled central nucleic acid complement comprises one detectable center label.

These and other aspects and embodiments of the invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, are incorporated herein by reference in their entirety, as if each was incorporated individually. Aspects of the invention can be modified, if necessary, to employ concepts of the various patents, applications and publications to provide yet further embodiments of the invention.

BRIEF DESCRIPTION OF THE SEVERAL VIEWS OF THE DRAWINGS

FIG. 1A shows the cluster configuration using open circles to indicate cluster locations; FIG. 1B shows a representation of an image that would be produced if all of the nucleic acids in the clusters are labeled; FIG. 1C shows the cluster configuration with the locations of cluster centers indicated by a black dot; FIG. 1D shows a representation of an image that would be produced if only nucleic acids located at a central location of each cluster are labeled; FIG. 1E shows a representation of an image that would be produced if nucleic acids located at a central location of each cluster lack a label that is present on nucleic acids surrounding each central location.

DETAILED DESCRIPTION

Figure 1:
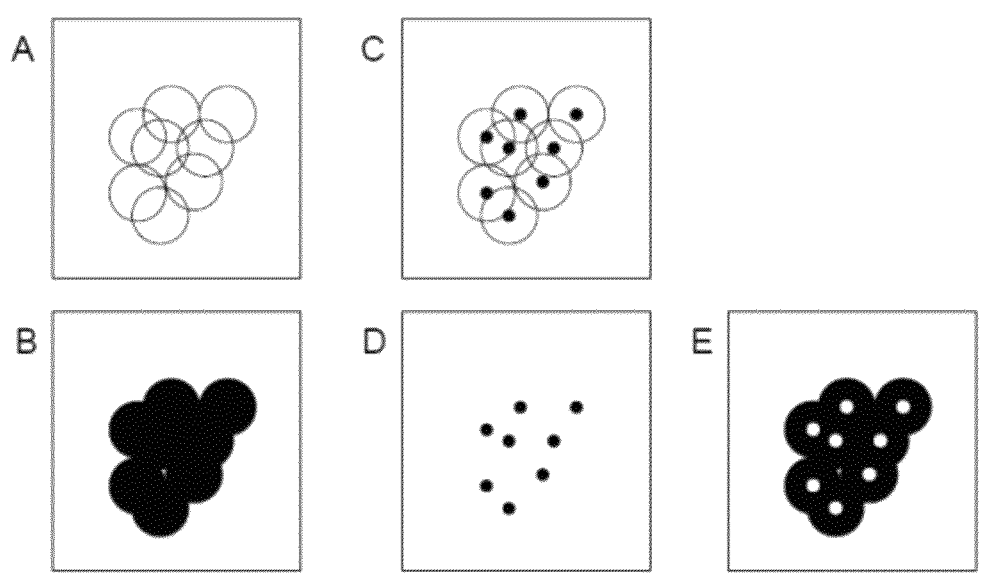
FIG. 1 shows closely packed nucleic acid clusters on a surface in the following configurations.
Figure 2:
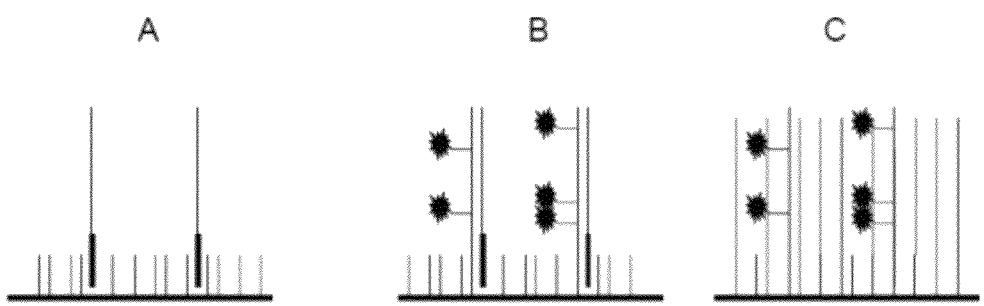
FIG. 2 shows an embodiment of the invention used to label the center of a nucleic acid cluster. A template is hybridized to a surface (FIG. 2A); the hybridized template is extended using labeled nucleotides to make a nucleic acid complement (FIG. 2B); and the nucleic acid complement is amplified using unlabelled nucleotides to produce a cluster with an identifiable center (FIG. 2C). The strands of adjacent clusters may overlap on the surface, but the initial strands remain discrete, and can therefore be used to locate the adjacent clusters of different sequence.

The present invention is directed in certain embodiments as described herein to a solid-phase immobilized nucleic acid cluster having an identifiable center, to methods for producing such a nucleic acid cluster, and to a method for annotating a center position in such a cluster. These and related embodiments will find uses in improving the quality and quantity of nucleic acid sequence information that can be obtained from a nucleic acid sample such as a nucleic acid template or its complement as described herein, for instance, a DNA or RNA polynucleotide or other nucleic acid sample. Accordingly, certain embodiments as disclosed herein may provide higher throughput polynucleotide sequencing, for instance, higher rates of collection of DNA or RNA sequence data, greater efficiency in sequence data collection, and/or lower costs of obtaining such sequence data, relative to previously available methodologies.

Certain embodiments as disclosed herein for the first time are based in part on heretofore unappreciated advantages that are obtained by producing a nucleic acid cluster having an identifiable center. For example, a center-labeled nucleic acid cluster can be provided by generating, on a solid support, an immobilized nucleic acid complement of a nucleic acid template such that at least one of the template and the complement comprises a detectable label; and amplifying the template and the complement to obtain a solid-phase immobilized nucleic acid cluster having (i) a substantially central location in which the detectable label is present to provide an identifiable center, and (ii) a surrounding region comprising immobilized copies of the template and of the complement.

Alternatively, a nucleic acid having an identifiable center can be provided by generating, on a solid support, an immobilized nucleic acid complement of a nucleic acid template such that at least one of the template and the complement lacks a particular detectable label; and amplifying the template and the complement to obtain a solid-phase immobilized nucleic acid cluster having (i) a substantially central location in which the detectable label is absent, and (ii) a surrounding region comprising immobilized copies of the template and of the complement that have the particular detectable label to provide an identifiable center. Thus, the cluster may in these and related embodiments appear to have a ring or donut shape, and the center can be distinguished due to the absence of a detectable label that is present in the surrounding region.

Without wishing to be bound by theory, these and related embodiments are believed to relate in part to unexpected advantages associated with a nucleic acid cluster that results from radially outward growth of the cluster in all directions from the identifiable and substantially central location at which the initial generation of the complement of the template occurs. Accordingly, and surprisingly, such embodiments advantageously afford a nucleic acid cluster having an identifiable center, for example, by virtue of the detectable label serving as a beacon that marks the center of the cluster (e.g., a detectable center label as provided herein). Hence, where, prior to the present disclosure, a solid-phase immobilized nucleic acid cluster as provided herein, grown in a substantially symmetrical and progressively outward manner from a specifically identified substantially central originating location, was neither contemplated nor predicted to confer any particular benefit, there is advantageously described herein for the first time a method for producing a nucleic acid cluster having an identifiable center, along with methods for using such a center-labeled nucleic acid cluster.

As described in greater detail herein, by exploiting the presently disclosed ability to identify the center position of a nucleic acid cluster, solid phase supports bearing high-density arrays of clusters can be produced from which useful nucleic acid sequence information can be obtained, where determination of the center position for adjacent, abutting or overlapping clusters, or for clusters from which overlapping or otherwise conflicting signals may emanate, permits unambiguous assignment of sequence information to its proper source cluster.

Accordingly and for example, the embodiments described herein identify the center of a solid-phase nucleic acid cluster and therefrom will permit the development of image processing software, as used to analyze optical signals that are generated during sequencing of such clusters, to discriminate unambiguously between two adjacent, abutting or overlapping clusters in order to assign a sequencing signal to a single, discrete source cluster. These and related embodiments thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain embodiments there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed embodiments will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

Nucleic Acids

In certain embodiments, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

The terms "nucleic acid", "nucleic acid molecule", and "polynucleotide" are used essentially interchangeably herein. In various embodiments, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain embodiments include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other embodiments, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular embodiments, a nucleic acid may have one or more detectable labels, as described elsewhere herein.

In particular embodiments, the nucleic acid to be used as a template or to be amplified, sequenced, analyzed, or otherwise used in a method set forth herein, can be at least 10, at least 20, at least 30, at least 40, at least 50, at least 50, at least 100, at least 150, at least 200, at least 250, at least 500, or at least 1000 nucleotides in length. In other particular embodiments, the nucleic acid can be about 150 to about 4000 nucleotides in length, about 500 to about 3000 nucleotides in length, or about 1000 to about 2000 nucleotides in length. Alternatively or additionally, a nucleic acid can be at most 100, at most 250, at most 500, at most 1000, at most 5000, at most 10,000, or at most 100,000 nucleotides in length.

The terms "isolated nucleic acid", "isolated polynucleotide", and "isolated nucleic acid molecule" are used interchangeably herein and refer to nucleic acid that is substantially or essentially free from components that normally accompany it in its native state, e.g., polypeptides, cells, organisms, etc. In certain embodiments an "isolated nucleic acid" may be a nucleic acid that has been purified from the nucleotide sequences which flank it in a naturally-occurring state, e.g., a DNA fragment that has been separated or removed from the sequences that are normally adjacent to the fragment. In another embodiment, an "isolated nucleic acid" may refer to a nucleic acid that has been extracted from, or separated or otherwise obtained from a cell, tissue, or organism such that it is no longer present in the cell, tissue or organism in its natural state.

It will be appreciated that nucleic acids of the present invention may be obtained from any biological sample from a subject or biological source. Biological samples may therefore include a blood sample, biopsy specimen, tissue explant, organ culture, biological fluid or any other tissue or cell preparation, or fraction or derivative thereof or isolated therefrom, from a subject or a biological source. The subject or biological source may be a human or non-human animal, including mammals and non-mammals, vertebrates and invertebrates, and may also be any other multicellular organism or single-celled organism such as a eukaryotic (including plants and algae) or prokaryotic organism, archaeon, microorganisms (e.g. bacteria, archaea, fungi, protists, viruses), aquatic plankton, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, nucleic acids may be obtained from primary cells, cell lines, freshly isolated cells or tissues, frozen cells or tissues, paraffin embedded cells or tissues, fixed cells or tissues, and/or laser dissected cells or tissues. In certain embodiments, the nucleic acids may be derived, purified, or isolated from any known prokaryotic or eukaryotic organism or virus.

Exemplary prokaryotes include, but are not limited to, *Escherichia coli*, and species of *Salmonella, Enterobacter, Camplyobacter, Stapylococcus, Pseudomonas*, and *Listeria*.

Exemplary eukaryotes include, but are not limited to, humans and non-human primates such as baboons, gorillas, chimpanzees, rhesus macaques and other non-human primates, and also include equine, bovine, sheep (ovine), goat (caprine), pig (porcine), dog (canine), cat (feline), chicken, rat, and mouse (murine) species; other non-limiting examples of eukaryotes include *Xenopus laevis, Danio rerio, Drosophila melanogaster, Caenorhabditis elegans*, and yeast species (e.g., *Saccharomyces, Schizosaccharomyces, Clamydia*). Other exemplary eukaryotes include plants such as *Arabidopsis thaliana*, barley, citrus fruits, cotton, grapes, wheat, tomato, potato, sugar cane, maize, tobacco, poplars, rice, and soybean.

Exemplary viruses include, but are not limited to, adenoviruses, herpesviruses, poxviruses, parvoviruses, reoviruses, picornaviruses, togaviruses, orthomyxoviruses, rhabdoviruses, retroviruses (e.g., lentiviruses), and hepadnaviruses. Other exemplary viruses include human immunodeficiency viruses and influenza viruses.

Nucleotides and Nucleosides

The term "nucleotide" refers to a heterocyclic nitrogenous base in N-glycosidic linkage with a phosphorylated sugar. Nucleotides are understood to include natural bases (standard), and a wide variety of art-recognized modified bases. Such bases are generally located at the 1' position of a nucleotide sugar moiety. Nucleotides generally comprise a base, sugar and a phosphate group. In RNA, the sugar is a ribose, and in DNA the sugar is a deoxyribose, i.e., a sugar lacking a hydroxyl group that is present in ribose. The nitrogenous base is a derivative of a purine or a pyrimidine. The purines are adenosine (A) and guanidine (G), and the pyrimidines are cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. The term "nucleoside" refers to a heterocyclic nitrogenous base in N-glycosidic linkage with a sugar. Nucleosides are recognized in the art to include natural bases (standard), and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

The terms "modified base" and "modified nucleotide" are used interchangeably herein and refer to nucleotide bases other than adenine, guanine, cytosine, thymine, and uracil at the 1' position or their equivalents; such bases can be used at any position, for example, within the catalytic core of an enzymatic nucleic acid molecule and/or in the substrate-binding regions of the nucleic acid molecule. The nucleoside residues of a nucleic acid may be coupled to each other by any of the numerous known internucleoside linkages. Such internucleoside linkages include, for example and without limitation, phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate, and sulfone internucleotide linkages. Nucleic acids may contain a non-natural sugar moiety in the backbone. Exemplary sugar modifications include but are not limited to 2' modifications such as addition of halogen, alkyl, substituted alkyl, allyl, aryl, O-alkyl or O-aryl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloallyl, heterocycloallcaryl, aminoallylamino, polyallylamino, phosphate, substituted phosphate, substituted silyl, and the like. Similar modifications can also be made at other positions on the sugar, particularly the 3' position of the sugar on the 3' terminal nucleotide and the 5' position of the 5' terminal nucleotide. In certain embodiments, oligonucleotides may comprise polymers such as peptide nucleic acids (PNA) and locked nucleic acids (LNA).

Exemplary chemically modified and other natural nucleic acid bases that can be introduced into nucleic acids include, but are not limited to, inosine, dihydrouridine, hypoxathanine, isocytosine, isoguanine, N6-methyladenosine, pseudouracil, pyridin-2-one, pyridin-4-one, quesosine, threonine derivatives, uridine-5-oxyacetic acid, wybutosine, wybutoxosine, xathanine, β-D-galactosylqueosine, β-D-mannosylqueosine, 2,2-dimethylguanosine, 15-halocytosine, 15-halouracil, 1-methyladenosine, 1-methylinosine, 2-aminoadenine, 2-methyladenosine, 2-methylguanosine, 2-methylthio-N-6-isopentenyladenosine, 2-propyl adenine, 2-propyl guanine, 2-thiocytidine, 2-thiocytosine, 2-thiothymine, 2-thiouracil, 2-thiouridine, 3-deazaadenine or the like, 3-deazaguanine, 3-methyl uracil, 3-methylcytidine, 3-nitropyrrole, 4-acetyltidine, 4-thiouracil, 4-thiouridine, 5-(carboxyhydroxymethyl)uridine, 5-carboxymethylaminomethyl-2-thiouridine, 5-alkylcytidines (e.g., 5-methylcytidine), 5-alkyluridines (e.g., ribothymidine), 5-carboxymethylaminomethyluridine, 5-halo substituted uracil or cytosine, 5-halouridine (e.g., 5-bromouridine) or 6-azapyrimidines or 6-alkylpyrimidines (e.g., 6-methyluridine), 5-hydroxymethyl cytosine, 5-methoxyaminomethyl-2-thiouridine, 5-methyl-2-thiouridine, 5-methylaminomethyluridine, 5-methylcarbonylmethyluridine, 5-methylcytosine, 5-methyloxyuridine, 5-nitroindole, 5-propynyl cytosine, 5-propynyl uracil, 5-uracil, 6-azo cytosine, 6-azo thymine, 6-azo uracil, 6-methyl adenine, 6-methyl guanine, 7-deazaadenine, 7-deazaguanine, 7-methyladenine, 7-methylguanine, 7-methylguanosine, 8-amino adenine or guanine, 8-azaadenine, 8-azaguanine, 8-halo adenine or guanine, 8-hydroxyl adenine or guanine, 8-thioalkyl adenine or guanine, 8-thiol adenine or guanine or the like. In a particular embodiment, isocytosine and/or isoguanine may be used in a nucleic acid in order to reduce non-specific hybridization, as generally described in U.S. Pat. No. 5,681,702. Further examples of chemically modified nucleotides that can be used in the methods and compositions of the present invention are those set forth below in the context of sequencing methods.

Template Nucleic Acid

As used herein, the terms "template nucleic acid" and "nucleic acid template" are used interchangeably and refer to the nucleic acid to be amplified, copied, sequenced, and/or otherwise analyzed. In certain embodiments the nucleic acid template may be in a single-stranded form, and in other embodiments, the nucleic acid template to be amplified, copied, sequenced, and/or otherwise analyzed may be provided in a double stranded form. In certain embodiments, the template nucleic acid comprises a target nucleic acid, and in certain embodiments the template nucleic acid may comprise a target nucleic acid and in addition, one or more non-target nucleic acid sequences. In related embodiments, the nucleic acid to be amplified, copied, sequenced, and/or otherwise analyzed comprises the target nucleic acid in single or double stranded form.

In particular embodiments, the template nucleic acid may be at least 10, at least 20, at least 30, at least 40, at least 50, at least 50, at least 100, at least 150, at least 200, at least 250, at least 500, or at least 1000 nucleotides in length. In other particular embodiments, the nucleic acid template may be about 150 to about 4000 nucleotides in length, about 500 to about 3000 nucleotides in length, or about 1000 to about 2000 nucleotides in length. Certain embodiments contemplate a nucleic acid template of at most 100, at most 250, at most 500, at most 1000, at most 5000, at most 10,000, or at most 100,000 nucleotides in length.

Nucleic acid templates may be prepared using a variety of standard techniques available and known to those skilled in the art. Exemplary methods of template preparation include, but are not limited to, those described in U.S. Pat. No. 7,115,400 and U.S. Patent Application Publication numbers 2005/0100900, 2005/0059048, 2007/0110638 and 2007/0128624, each of which is herein incorporated by reference in its entirety. The nucleotides making up the nucleic acid templates may be naturally occurring or non-naturally occurring nucleotides. In particular embodiments, a nucleic acid template may comprise one or more detectable labels, as described elsewhere herein. The one or more detectable labels may be attached to the nucleic acid template at the 5' end, at the 3' end, and/or at any nucleotide position within the nucleic acid template. According to certain contemplated embodiments the nucleic acid templates of the invention not only may comprise the nucleic acid to be amplified and/or sequenced but may, in addition, optionally comprise short oligonucleotide sequences at the 5' and/or 3' end(s) of the template nucleic acid.

The term "oligonucleotide" refers to a polymer of two or more deoxyribonucleotides, ribonucleotides and/or naturally occurring or synthetic analogs and derivatives thereof. Persons familiar with the art will appreciate that any nucleic acid of the present invention may include engineered internucleoside linkages, modified sugars, and/or PNA/LNA.

In certain embodiments, oligonucleotide sequences may be adapters that are ligated to the 5' and/or 3' ends of a nucleic acid. In other certain embodiments, oligonucleotide sequences may already be present in the nucleic acid to be used as a template. In certain particular embodiments, adapters or other olignucleotide sequences may comprise one or more detectable labels, as described elsewhere herein. The one or more detectable labels can be attached at the 5' end, at the 3' end, and/or at any nucleotide position within the adapter or oligonucleotide sequence.

For example, the oligonucleotide sequence located at the 5' end of a nucleic acid template in certain embodiments may be referred to as "Y". Oligonucleotide sequence Y can be of a known or unknown sequence or a suitable combination thereof and can be of variable length. In particular illustrative embodiments, for example, oligonucleotide sequence Y is 5, 10, 15, 20, 25, 30 or more nucleotides in length. In other embodiments, oligonucleotide sequence Y is between about 5 and about 100 nucleotides in length, between about 10 and about 50 nucleotides in length, between about 10 and about 30 nucleotides in length, or between about 5 and about 25 nucleotides in length, or any intervening range lengths thereof. In certain embodiments, oligonucleotide sequence Y is approximately 15, 16, 17, 18, 19, 20, 21, 22, 23, 24, or 25 nucleotides in length. Naturally occurring and/or non-naturally occurring nucleotides may be present in the oligonucleotide sequence Y.

In one embodiment, the oligonucleotide sequence located at the 3' end of a nucleic acid template may be referred to as "Z". Oligonucleotide sequence Z can be of a known or unknown sequence or a suitable combination thereof and can be of variable length. For example, in particular illustrative embodiments, oligonucleotide sequence Z is 5, 10, 15, 20, 25, 30 or more nucleotides in length. In other embodiments, oligonucleotide sequence Z is between about 5 and about 100 nucleotides in length, between about 10 and about 50 nucleotides in length, between about 10 and about 30 nucleotides in length, or between about 5 and about 25 nucleotides in length, or any intervening range lengths thereof. In certain embodiments, oligonucleotide sequence Z is approximately 15, 16, 17, 18, 19, 20, 21, 22, 23, 24, or 25 nucleotides in length. Naturally occurring and/or non-naturally occurring nucleotides may be present in the oligonucleotide sequence Z.

The oligonucleotide sequences Y and Z located at the 5' and 3' ends, respectively, of a nucleic acid template need not be localized at the extreme ends of the template. In one embodiment, the oligonucleotide sequences Y and/or Z may be located at or near the 5' and 3' ends of a nucleic acid template, respectively. For example, oligonucleotide sequences Y and/or Z may be within 0 to 100 nucleotides, within 5 to 50 nucleotides, or within 10 to 25 nucleotides of the 5' and 3' ends. In certain embodiments, oligonucleotide sequences Y and/or Z may be located more than 50, more than 75, or more than 100 or more nucleotides away from the 5' and 3' termini of the nucleic acid template. It will be appreciated that the oligonucleotide sequences Y and Z may therefore be located at any position within the nucleic acid template. The sequences Y and Z are typically on opposing sides, i.e., flanking, a nucleic acid sequence which is to be amplified and/or sequenced. The skilled artisan would also recognize that sequences Y and Z need not be equidistant from the 5' and 3' termini of the nucleic acid template, respectively. Adapters and oligonucleotide sequences, such as the oligonucleotide sequences Y and Z exemplified above, can be universal sequences. Universal sequences and their use for forming priming sites for universal primers are set forth in further detail below.

In particular embodiments, wherein the nucleic acid template is in a double stranded form, the oligonucleotide sequences Y and Z are contained at the 5' and 3' ends, respectively, of one of the strands. The other strand, due to the base pairing rules of DNA, is complementary to the strand containing oligonucleotide sequences Y and Z and thus, contains an oligonucleotide sequence Z' at the 5' end and an oligonucleotide sequence Y' at the 3' end.

Nucleic Acid Complement

As used herein, the terms "complementary" and "complementarity" refer to nucleic acids (i.e., a sequence of nucleotides) that are related by Watson-Crick base-pairing rules according to convention in the molecular biology art. Two nucleotides that are on opposite (i.e., with respect to 5'/3' sugar-phosphate backbone polarity) complementary nucleic acid strands and that are connected to one another via hydrogen bonds are called a base pair (often abbreviated bp). In the canonical Watson-Crick base pairing, adenine (A) forms a base pair with thymine (T), as does guanine (G) with cytosine (C) in DNA. In RNA, thymine is replaced by uracil (U). For example, the nucleotide adenine is complementary to thymine. For example, the DNA sequence "A-G-T," is complementary to the DNA sequence "T-C-A" or the RNA sequence "U-C-A". Complementarity can be "partial," in which only some of the nucleic acids' bases are paired according to the base pairing rules. Or, there may be "complete" or "total" complementarity between the nucleic acids. The degree of complementarity between nucleic acid strands has significant effects on the efficiency and strength of hybridization between nucleic acid strands.

"Complementary nucleic acid", "nucleic acid complement", and "central nucleic acid complement" are used substantially interchangeably and refer to a nucleic acid complement or complementary nucleic acid that is complementary to a reference nucleic acid, such as a template nucleic acid. In certain embodiments, a nucleic acid complement may be generated by "primer extension", e.g., extending an oligonucleotide primer by polynucleotide polymerase-catalyzed serial incorporation, proceeding in a 5'-to-3' direction, into the thus-extended primer of individual nucleotides that are complementary to those of an antiparallel (e.g., 3'-to-5') template nucleic acid sequence, wherein the primer is attached at its 5' end to a solid support and hybridized to the nucleic acid template. In related embodiments, nucleic acid complements thus may be immobilized to a solid support at their 5' ends. In certain further related embodiments, copies of the immobilized nucleic acid complement(s) may be generated by performing nucleic acid amplification (e.g., primer extension, thermal polymerase chain reaction, isothermal polymerase chain reaction, or other nucleic acid amplification methodologies). The nucleic acid complement may comprise any combination of natural and/or non-natural nucleotides, e.g., nucleotide derivatives or analogs.

As also described elsewhere herein, an immobilized nucleic acid complement may advantageously comprise one or more detectable labels. The one or more detectable labels may be attached at the 5' end, at the 3' end, and/or at any nucleotide position within the immobilized nucleic acid complement. For example, an immobilized primer may be extended, by primer extension along a nucleic acid template, with a first nucleotide that comprises one or more detectable labels, thereby generating a detectably labeled nucleic acid complement. In a related embodiment, the immobilized primer may be extended by a primer extension reaction in which is included a mixture of nucleotides, wherein one or more of the nucleotides comprises one or more labels, thereby generating a detectably labeled nucleic acid complement.

In one non-limiting example, for the generation of an immobilized nucleic acid complement, an immobilized primer may be extended by a primer extension reaction using a nucleotide mix comprising unlabeled dATP, dTTP, and dGTP and detectably labeled dCTP. The mixture may also comprise both labeled dCTP and unlabeled dCTP including, for example, as a mixture having a lesser amount of unlabeled dCTP relative to the amount of labeled dCTP. For instance, the amount of unlabeled dCTP may be present in $\frac{1}{10,000}$, $\frac{1}{1,000}$, $\frac{1}{100}$, $\frac{1}{20}$, $\frac{1}{10}$, $\frac{1}{5}$, $\frac{1}{3}$, or $\frac{1}{2}$ the relative amount of the labeled dCTP in the primer extension reaction. Alternatively, multiple labeled nucleotides may be present in the primer extension reaction for incorporation into the nucleic acid complement. For example, in the generation of an immobilized nucleic acid complement, a primer may be extended using a nucleotide mix comprising unlabeled dTTP and dGTP and detectably labeled dATP and dCTP. As another example, any one, two, three, or all four of dATP, dTTP, dGTP and dCTP may be detectably labeled and incorporated into the extended primer to effect the generation of a detectably labeled immobilized nucleic acid complement. Different labeled nucleotides used in a mixture, such as those exemplified above, can have the same label or, alternatively, different labels can be present on the different labeled nucleotides.

Nucleic Acid Clusters

"Nucleic acid cluster" and "nucleic acid colony" are used interchangeably and refer to a plurality of copies of a nucleic acid template and/or complements thereof attached to a solid support. Typically and in certain preferred embodiments, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. In a particular embodiment, the diameter of a nucleic acid cluster is about 0.5 µm, about 1 µm, about 1.5 µm, about 2 µm, about 2.5 µm, about 3 µm, about 4 µm, about 5 µm, or about 6 µm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, 100,000/mm² to 1,000,000/mm² and 1,000,000/mm² to 10,000,000/mm².

As disclosed herein, a nucleic acid cluster may comprise (a) a substantially central location as provided herein, comprising at least one nucleic acid template and at least one nucleic acid complement thereof, and (b) a surrounding region comprising one or more immobilized copies of the at least one nucleic acid template and of the at least one nucleic acid complement thereof, the surrounding region comprising that portion of the cluster that is outside of the substantially central location. In certain preferred embodiments, within the substantially central location either or both of the nucleic acid template and the nucleic acid complement thereof comprise a detectable label, such that the nucleic acid cluster has an identifiable center as also discussed elsewhere herein.

Accordingly, in certain preferred embodiments, there is contemplated, immobilized on a solid support as provided herein, one or a plurality of nucleic acid clusters that each have an identifiable center. Without wishing to be bound by any particular theory, it is believed that nucleic acid clusters are generated by the geometric and radial nucleic acid amplification of a single immobilized nucleic acid template and/or a single immobilized nucleic acid complement of the template (i.e., the original nucleic acid template and the original complement thereof). Thus, detectably labeling the immobilized nucleic acid template and/or the initial nucleic acid complement permits ready identification of the center of a nucleic acid cluster generated therefrom.

Identifiable Center of a Nucleic Acid Cluster

The identifiable center of a nucleic acid cluster comprises one or more nucleic acids in a cluster that can be distinguished from surrounding nucleic acids in the same cluster. Typically, the one or more nucleic acids in the identifiable center and the surrounding nucleic acids share a common sequence, for example, by being copies of a common template nucleic acid or of a nucleic acid complement of the template nucleic acid. In particular embodiments, the nucleic acids in the center region of a cluster may include nucleotide analogs that are different from the nucleotide analogs found in nucleic acids present in the surrounding region. For example, nucleic strands in the center region of a cluster can include uracil nucleotides at one or more position in a sequence whereas strands in the surrounding region can have thymine nucleotides at the one or more positions in the sequence. Other analog pairs such as guanine and 8-oxo guanine find similar use.

The identifiable center of a nucleic acid cluster may in certain embodiments comprise the original template nucleic acid and the original immobilized complement thereof, either of which, or both, can be detectably labeled. In other embodiments, the identifiable center of a nucleic acid cluster may comprise a detectably labeled nucleic acid complement and/or a detectably labeled template nucleic acid and/or detectably labeled copies thereof.

The identifiable center of a nucleic acid cluster may comprise a detectably labeled nucleic acid complement of a nucleic acid template and/or detectably labeled copies thereof. In certain embodiments, 1, 2, 3, 4, 5, 6, 7, 8, 9, or more copies of the nucleic acid complement may be detectably labeled with a detectable label as provided herein. In certain other embodiments, less than 25, less than 20, less than 15, less than 10 or less than 5 copies of the nucleic acid complement may be detectably labeled. Additionally or alternatively, the identifiable center of a nucleic acid cluster may in certain embodiments comprise a detectably labeled nucleic acid template and/or detectably labeled copies thereof. In certain embodiments, 1, 2, 3, 4, 5, 6, 7, 8, 9, 10 or more copies of the nucleic acid template may be detectably labeled. In other certain embodiments, less than 25, less than 20, less than 15, less than 10 or less than 5 copies of the nucleic acid template are labeled.

The identifiable center of a nucleic acid cluster may be identified by detecting a detectably labeled nucleic acid complement and/or a detectably labeled template nucleic acid and/or detectably labeled copies thereof, using a suitable imaging means, for example, a confocal imaging device or a charge coupled device (CCD) camera. Exemplary imaging devices, include, but are not limited to those described in U.S. Pat. No. 7,329,860; U.S. Pat. No. 5,754,291; U.S. Pat. No. 5,981,956 and U.S. Ser. No. 12/295,337, each of which is herein incorporated by reference in its entirety.

It will be appreciated that the imaging means may be used to determine a reference position in a nucleic acid cluster or in a plurality of nucleic acid clusters on the solid support, such as the location, boundary, diameter, area, shape, overlap and/or center of one or a plurality of solid-phase immobilized nucleic acid clusters (and/or of a detectable signal originating therefrom), and that such reference position may be recorded, documented, annotated, converted into an interpretable signal, or the like, as may appropriately yield meaningful information depending on the methodologies and instrumentation being employed. For example, the reference position can be interpreted by the imaging device as a signal that may be generated from a labeled center in a cluster, from a surrounding region within the cluster, and/or from two or more adjacent, abutting or overlapping clusters. The signal may, for instance, take the form of a detectable optical signal emanating from a defined and identifiable location, such as a fluorescent signal, or may be a detectable signal originating from any other detectable label as provided herein.

Certain embodiments contemplate determination of a reference position by identification of physical locations on the solid support that lack a detectable label, such as (in certain embodiments) the surrounding region that surrounds the substantially central location in an immobilized nucleic acid cluster. The reference position thus may identify the actual physical position of the substantially central location within the cluster, or of the surrounding region within the cluster which surrounding region surrounds the substantially central location in the cluster, or of two or more overlapping clusters that are immobilized on the solid support, depending on the particular format that is being employed according to the disclosure herein.

According to these and related embodiments as will be apparent to the skilled person in view of the present disclosure, the referenced position of a signal generated from a substantially central location of a cluster, and/or from another location in an immobilized nucleic acid cluster, and/or from two or more overlapping clusters, may be used to determine the actual physical position on the solid support of the center, and/or of the cluster, and/or of two or more adjacent, abutting or overlapping clusters, which may be understood typically to include immediately proximate or adjacent clusters from which signals emanate in a manner that precludes ready identification of the single source cluster for a given signal, e.g., overlapping signals.

The position of the identifiable center may be determined and recorded prior to, during or after, amplification of the detectably labeled nucleic acid complement and/or of the detectably labeled template nucleic acid, which amplification takes place as a step in the presently described methods for producing a nucleic acid cluster having an identifiable center, including in certain embodiments methods which further comprise performing one or more nucleic acid sequencing steps. In yet other embodiments, the position of the identifiable center (i.e., the origin of the cluster as identified by detection of the detectable label that may be a component of the nucleic acid template or of the immobilized nucleic acid complement of such template, or that may be a component of both) is determined and recorded before any nucleic acid amplification step takes place, and optionally also after each of one or a plurality of amplification reactions that amplify the nucleic acid complement, the nucleic acid template, and/or copies thereof. In this manner, the center of the nucleic acid cluster, comprising at least one detectably labeled nucleic acid, can be distinguished from surrounding copies that are not labeled, or that may have a different detectable label.

Alternatively, the substantially central location in a cluster (e.g., the site where reside the nucleic acid template and the nucleic acid complement thereof, at least one of which is detectably labeled) may be distinguished due to the absence therefrom of a signal for a distinct label that is present only in the surrounding nucleic acid copies. Absence of a signal for a label can be due to the absence of the label from the location being detected or absence of signal can be due to an agent that quenches or masks the label, thereby preventing or inhibiting detection of the label. In related further embodiments, the position of the identifiable center may be determined and recorded before commencing, or during each of one or a plurality of sequencing steps as provided herein, which sequencing steps are present in a method that comprises determining the nucleotide sequence of the nucleic acid template and/or of the nucleic acid complement thereof in an immobilized nucleic acid cluster.

In an exemplary embodiment, the identifiable center of a cluster may be made by carrying out the first cycles of template amplification using a nucleoside analog which is not used in the later amplification cycles. As such, the nucleoside analog is incorporated into nucleic acid strands in the center region of the cluster but not in nucleic acid strands which form the surrounding region. For example, nucleosides such as uracil or 8-oxo-guanine can be used to selectively form strands in the central location of the clusters that contain uracil or 8-oxo-guanine bases respectively, while the strands in the surrounding region lack uracil or 8-oxo-guanine. The clusters can be treated to selectively remove the nucleic acids in the central location while leaving those in the surrounding region. Continuing with the example of a cluster having uracil or 8-oxo-guanine bases in the nucleic acids of the central location, the clusters can be treated to remove the uracil or 8-oxo-guanine bases from their sugars. This will give rise to strands in the central location that have abasic sites which undergo strand cleavage in the presence of endonucleases while strands in the surrounding region are not cleaved. The resulting cluster will have a ring or donut shape.

Figure 3:
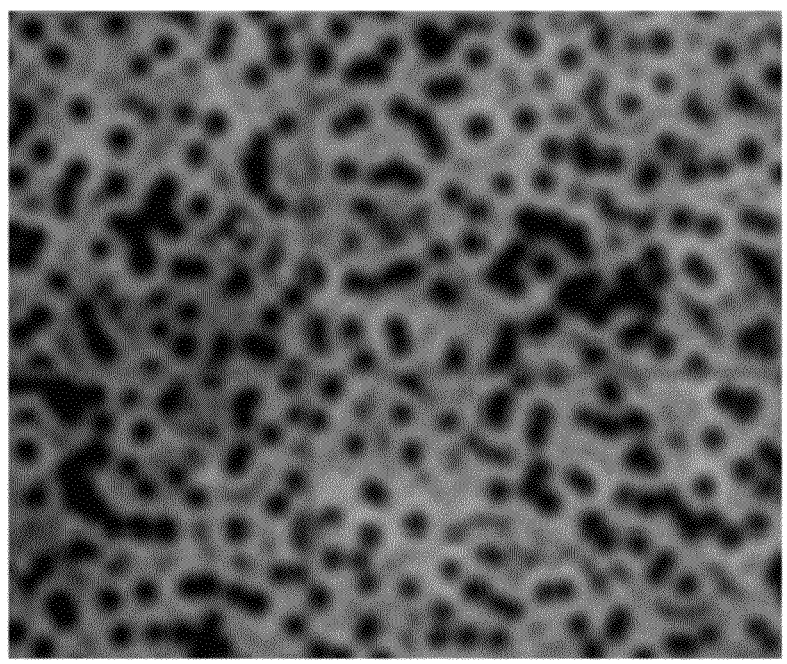
FIG. 3 shows an image of an array of clusters where the center of the cluster is unlabeled, the labeled surrounding region forming a ring of fluorescence around the unlabeled center. The center nucleic acids of the cluster were formed by extension using dUTP rather than dTTP. The nucleic acids containing dUTP were digested using Uracil DNA glyosylase, and hence the cluster appears as a ring rather than a sphere, as the centrally located strands were no longer present and hence were not capable of being labeled.

FIG. 3 shows an image of an array of clusters where the central location of each cluster appears darker than the surrounding region. The clusters were produced using dUTP plus dATP, dGTP and dCTP in the first few cycles of amplification, followed by dTTP, dATP, dGTP and dCTP in the remaining cycles. After cluster formation, the solid support was treated with USER (New England Biolabs, Ipswich, Mass.; product number M5505). The USER enzyme generates a single nucleotide gap at the location of a uracil. USER Enzyme is a mixture of Uracil DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. After USER treatment, the strands are thus modified such that they are not capable of being labeled by an intercalator stain (in this case Sybr Green). Similarly, the modified strands are not capable of undergoing hybridization with a sequencing primer, so are not detectable upon sequencing. The dark space on the image of FIG. 3 provided by the central regions can provide a fiducial marking for image registration or can provide a dark region useful for various focusing techniques.

The identifiable center of a nucleic acid cluster as provided by the compositions and methods described herein will be understood by those skilled in the art to include, in non-limiting fashion, the approximate geometric center, the approximate center of mass, or the centroid of a nucleic acid cluster. Thus, the approximate center would be understood to be substantially the center location of the nucleic acid cluster. As used herein, the terms "substantially center location", "substantially central location", "substantially central position", and "substantially center position" are used interchangeably and refer to a center location or position that is located at a site which comprises the at least 90%, 92%, 95%, 97% or 99% confidence interval of the geometric center, center of mass, or centroid of the nucleic acid cluster, as can be determined using available image analysis algorithms to assess statistical significance Images of nucleic acid clusters can be analyzed using image analysis software, for example, the image analysis software as implemented in the Illumina data analysis pipeline (Illumina, Inc., San Diego, Calif.). A cluster will typically approximate a circle shape, but it will be understood that clusters of other shapes can be used as well and that the methods set forth herein can be used for clusters of any of a variety of shapes.

The identifiable center, while being discrete, may also vary in size. In particular embodiments, the identifiable center comprises 1, 2, 3, 4, 5, 6, 7, 8, 9, 10, 15, 20, 25, or more labeled nucleic acids, each of which comprises one or more detectable labels. For example, the area of the identifiable center of a nucleic acid cluster can be between about $1/100,000^{th}$ to about $1/1,000,000^{th}$ of the nucleic acid cluster area, between about $1/10,000^{th}$ to about $1/100,000^{th}$ of the nucleic acid cluster area, between about $1/1,000^{th}$ to about $1/10,000^{th}$ of the nucleic acid cluster area, between about $1/100^{th}$ to about $1/1,000^{th}$ of the nucleic acid cluster area, or between about $1/10^{th}$ to about $1/100^{th}$ of the nucleic acid cluster area, or any intervening range thereof. In particular embodiments, the area of the identifiable center of a nucleic acid cluster can be at least about $1/100,000^{th}$, $1/10,000^{th}$, $1/1,000^{th}$, $1/100^{th}$, $1/10^{th}$, $1/5^{th}$, $1/3^{rd}$, or ½ of the nucleic acid cluster area. Alternatively or additionally, the area of the identifiable center of a nucleic acid cluster can be at most about $1/1,000,000^{th}$, $1/100,000^{th}$, $1/10,000^{th}$, $1/1,000^{th}$, $1/100^{th}$, $1/10^{th}$, $1/5^{th}$, $1/3^{rd}$, or ½ of the nucleic acid cluster area. One having skill in the art would understand that the size of the identifiable center can be limited, in part, by the number of nucleic acid amplification reactions performed on the central nucleic acid complement and/or the nucleic acid template.

Detectable Labels

Conventional detectable labels are contemplated for use in certain herein described embodiments to permit determination of the location of a nucleic acid such as a nucleic acid template and/or an immobilized complement thereof, and a large number of such labels are known for nucleic acid labeling, typically comprising chemical or biochemical moieties having known physicochemical and/or biochemical properties. Persons skilled in the art will appreciate that a detectable label may be a moiety the presence or absence of which can be ascertained with confidence and in a statistically significant manner relative to a suitable control, using state of the art instrumentation and methodologies.

Detection of a detectable label may be carried out by any suitable method as may be known according to the particular detectable label that is employed, including, as non-limiting examples, by fluorescence imaging or by other imaging means, such as by laser scanning confocal microscopy and/or by using a charge coupled device (CCD) camera. Imaging means suitable for determining fluorescent signals produced upon appropriate excitation by detectable labels that are fluorophores are described, for example, in PCT application number PCT/US2007/07991, which is herein incorporated by reference in its entirety.

In particular embodiments, one or more detectable label may be chemically conjugated to nucleic acid such as a template or primer. For example, a detectable label can be present on a template nucleic acid prior to attachment of the template to a surface and/or prior to amplification of the template to form a cluster. If desired, a primer used for one or more amplification steps, for example, in the early stages of cluster growth can include one or more detectable labels. Alternatively or additionally, nucleotides used during particular amplification steps, such as early steps of cluster growth, can contain a detectable label. Thus, a detectable label may be chemically conjugated to a naturally occurring or artificial nucleotide or to a nucleotide analog, a nucleotide derivative, or a modified or non-natural nucleotide.

Detectably labeled nucleic acids, nucleotides, derivatives, or analogs thereof may comprise one or more detectable labels. Detectably labeled primers or nucleotides may be incorporated into nucleic acids (e.g., by extension, polymerization, and/or ligation), to render the resulting nucleic acids detectable. Each strand of a nucleic acid generated by primer extension or nucleic acid amplification (e.g., thermal polymerase chain reaction or isothermal polymerase chain reaction, or other nucleic acid amplification strategies) may include 1, 2, 3, 4, 5, 6, 7, 8, 9, or 10 or more detectably labeled nucleotides. In certain embodiments, a nucleic acid generated by primer extension or nucleic acid amplification may comprises a single detectably labeled nucleotide, and in certain embodiments the nucleic acid may comprise at least one, at least two or more detectably labeled nucleotides. In other embodiments, a nucleic acid generated by primer extension or nucleic acid amplification comprises exclusively detectably labeled nucleotides. A nucleic acid generated by primer extension or nucleic acid amplification may comprise a single type of detectable labeled nucleotide such as, for example, a labeled form of A, G, C, T or U. In certain embodiments, 1, 2, 3, 4 or all of the nucleotides of a particular type may include a detectable label.

In particular embodiments, labeled nucleotides can be used exclusively in the initial cycles of extension in order to exclusively label the center location of a cluster. For example, labeled nucleotides may be used in the first and second cycles of extension, with subsequent cycles of extension/amplification performed using solely unlabelled nucleotides. For example, if the template strand being copied in the extension step contains 1000 nucleotide bases, 250 of each type of nucleotide (A, G, C and T/U), the strand generated upon extension may contain between 1 to 1000 labeled nucleotides. If the extension is carried out with labeled A nucleotides, and unlabelled G, C and T/U nucleotides, the extension product should contain 250 labels, one per incorporated A nucleotide. Using a 1/1 ratio of labeled to unlabeled A means that the strands should contain 125 labels, assuming equivalent incorporation kinetics for the two A nucleotides. Thus the clusters may contain a central labeled strand carrying multiple labels, surrounded by unlabelled strands.

In certain preferred embodiments the preferred detectable label is a fluorophore. Exemplary fluorophores, include, but are not limited to umbelliferone, fluorescein, fluorescein isothiocyanate, rhodamine, tetramethyl rhodamine (TMR), eosin, green fluorescent protein, erythrosin, coumarin, alexa, BODIPY, acridine, coumarin, benzanthracene, cyanins methyl coumarin, pyrene, malachite green, stilbene, lucifer yellow, Cascade Blue™, Texas Red, dichlorotriazinylamine fluorescein, dansyl chloride, phycoerythrin, fluorescent lanthamide complexes such as those including Europium and Terbium, Cy3, Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Haugland; Welch et al. (*Chem. Eur. J.* 5(3): 951-960, 1999); Zhu et al. (*Cytometry* 28:206-211, 1997); Prober et al. (*Science* 238:336-341, 1987); Connell et al. (*BioTechniques* 5(4):342-384, 1987); Ansorge et al. (*Nucl. Acids Res.* 15(11):4593-4602, 1987); and Smith et al. (*Nature* 321:674, 1986). Other commercially available fluorescent labels include, but are not limited to, FAM, HEX, TAMRA and Rox (see, e.g., Premstaller et al., 2002 *Genomics* 79(6):793). The fluorophores may be rhodamine or cyanine analogues, for example as described in WO 07/135,368 and U.S. Ser. No. 12/227,474. Example of commercially available fluorophores include those supplied by Atto-Tec GmbH (Siegen-Weidenau, Germany) or Dyomics GmbH (Jena, Germany). Fluorescent nanocrystals can be useful as well due to their relatively narrow excitation and emission profiles, which can be convenient for distinguishing from other dyes used in a particular method or technique.

Although fluorescent labels are preferred, other forms of detectable labels will be apparent to those skilled in the art, as useful in the herein disclosed compositions and methods. For example, in particular embodiments, the detectable label may comprise one or more of radionuclides, enzymes, chemiluminescent agents, and/or colorimetric or chromogenic agents. Nucleic acids and/or nucleotides comprising one or more of these or other detectable labels as provided herein may be referred to as being detectably labeled.

In other embodiments, detectable labels may include, but need not be limited to, radiolabels, quantum dot labels, detectable metal labels (e.g., gold, such as colloidal gold, silver), haptens (e.g., dinitrophenol, digoxigenin, biotin), chromophores, enzymes, affinity ligands, electromagnetic spin labels, heavy atom labels, nanoparticle light scattering labels or other labeled nanoparticles or spherical shells, and other signal generating labels known to those of skill in the art (see, for example, Empodocles, et al., *Nature* 399:126-130, 1999; Reichert et al., *Anal. Chem.* 72:6025-6029, 2000; and Lacoste et al., *Proc. Natl. Acad. Sci. USA* 97 (17):9461-9466, 2000. Affinity ligands can be detected, for example, by binding to a receptor having a detectable label. For example, the SAPE technique can be used in which nucleic acids having biotin are incubated with streptavidin-phycoerythrin (SAPE), followed by incubation with a biotinylated anti-streptavidin antibody, and finally incubation with SAPE again. Exemplary SAPE methods are described in U.S. Pat. No. 6,203,989, which is incorporated herein by reference.

Affinity ligands and receptors, when present as labels on nucleic acids according to the methods set forth herein, can be used to attach the nucleic acids to surfaces. For example, a template nucleic acid or complementary copy of a template that is chemically conjugated or otherwise attached to an affinity ligand or receptor can be attached to a surface via binding to a partner receptor or ligand on the surface.

Exemplary radiolabels include, but are not limited to $^{14}$C, $^{90}$Y, $^{123}$I, $^{124}$I, $^{125}$I, $^{131}$I, $^{186}$Re, $^{188}$Re, $^{211}$At, $^{212}$Bi, Tc99 m, $^{35}$S, and $^{3}$H.

Exemplary enzymes include, but are not limited to, readily detectable reporter enzymes, for example, enzymes having well characterized and readily available substrates from which detectable products can be generated, such as horseradish peroxidase, alkaline phosphatase, β-galactosidase, and acetylcholinesterase.

Multiple detectable labels may also be used in certain contemplated embodiments of the invention. For example, bi-fluorophore fluorescence resonance energey transfer (FRET) cassettes (*Tet. Letts.* 46:8867-8871, 2000) are well known in the art and may be utilized as detectable labels as provided herein. Multi-fluor dendrimeric systems (*J. Amer. Chem. Soc.* 123:8101-8108, 2001) may also be used.

Multi-component labels may also be used in certain of the herein described invention embodiments. A multi-component label is one which is dependent on the interaction with a further compound for detection. For example, a common multi-component label used in biology is the biotin-streptavidin system. Biotin may be used as a label attached to the nucleotide base. Streptavidin may then be added separately to enable detection of the location of the biotin to occur, which detection may proceed, for example, by providing streptavidin in the form of a fluorescent conjugate (e.g., fluorescein-streptavidin) or as an enzyme conjugate (e.g., horseradish peroxidase-streptavidin) or as a reagent that comprises another detectable label as provided herein. SAPE methods, such as those set forth above are another example of biotin-streptavidin systems. Other multi-component systems are available. For example, the chemical hapten dinitrophenol (DNP) has a number of specific commercially available fluorescent antibodies that may be used for detection, by a variety of immunochemical detection means, of detectably labeled molecules that comprise DNP as the detectable label.

Detectable Center Labels

As used herein, the term "detectable center label" refers to a detectable label, as described supra, that may be detected to identify a substantially central location of a nucleic acid cluster, for example, in the course of annotating the center position of the cluster. Preferably a detectable center label may be used to identify an identifiable center of a nucleic acid cluster as provided herein, such that in certain embodiments the detectable center label may be limited in its occurrence or distribution to a substantially central location in a cluster. A detectable center label may typically be selected so that it can be readily distinguished from any other detectable label(s) that may be used to mark other than the identifiable center of a cluster, such as labels used in nucleic acid sequencing within a cluster and/or labels situated in a surrounding region in a cluster, which surrounding region surrounds the substantially central location of the cluster. A center label can be a different molecule than those used as labels in sequencing. Alternatively, the label may be similar to, or identical to one or more of the labels used in sequencing. The label may be attached to the central region of the cluster in such a way that the label can be quenched or removed, for example, by chemical cleavage. Thus an image of the central region of the clusters can be recorded and the label removed before commencing sequencing. In such a configuration, the need for additional hardware on the sequencing system may be removed.

A detectable center label may be incorporated into the nucleotide sequence of the original nucleic acid template and/or the original immobilized nucleic acid complement thereof, so as to allow the identification of the identifiable center of a nucleic acid cluster. In particular embodiments, one or more detectable center labels may be incorporated into one or a plurality of copies of the template nucleic acid and/or immobilized nucleic acid complement thereof. In certain embodiments, the detectable center label may be incorporated into 1, 2, 3, 4, 5, 6, 7, 8, 9, 10, 20, 25, 50 or more copies of the template nucleic acid and/or immobilized nucleic acid complement thereof. In certain embodiments labeled nucleotides may be incorporated in the first and second amplification cycles such that both primer 1 and primer 2 are extended using labeled nucleotides in each cluster. If primer 1 or primer 2 contains a cleavage site for subsequent cluster linearization, use of labeled nucleotides in two or more cycles avoids loss of labeled strand upon linearization which could otherwise result if only the first extension cycle uses labeled nucleotides.

In embodiments where labeled nucleotides are incorporated, the label may be attached to the nucleotide through a cleavable linker. Some useful nucleotides with cleavable linkers are described in U.S. Pat. No. 7,414,116 and U.S. Pat. No. 7,057,026, the contents of which are incorporated by reference herein in their entirety. Examples of cleavable linkers include chemically cleavable linkers, photochemically cleavable linkers or enzyme cleavable linkers. Chemically cleavable linkers may include linkers containing an allyl, disulfide or azido moiety. A linker may be cleaved after determining the central location of a cluster, and the cleaving step can occur before or after a first cycle of sequencing. In particular embodiments, a linker used to identify a central location may be of the same moiety as a linker which attaches a base to a detectable label of the nucleotides used in sequencing. An advantage of using the same linker for identifying a central location and for sequencing steps is that a single cleavage treatment may remove both the sequencing label and the central label from the clusters.

The detectable center label identifies a substantially central location or center of the cluster. In certain embodiments, one or a plurality of copies of the template nucleic acid, and/or of the immobilized nucleic acid complement thereof, surround the substantially central location or center of the nucleic acid cluster and are not detectably labeled. In certain related embodiments, the one or a plurality of copies of the template nucleic acid, and/or of the immobilized nucleic acid complement thereof, surround the substantially central location or center of the nucleic acid cluster and comprise a detectable label that is detectably distinct from (i.e., can be readily discerned from) the detectable center label. Two detectable labels that are detectably distinct may be readily discerned from one another by methodologies with which the skilled person will be familiar.

For instance, if two detectable labels are both fluorophores, the skilled person can select two or more different fluorophores that are detectably distinct by virtue of their having readily distinguishable excitation/emission spectra, such that appropriate detection means (e.g., excitation energy sources, defined band-pass filters, sensors tuned to specific emissions wavelengths or wavelength ranges, photomultiplier tubes, etc.) can be selected to afford unambiguous discrimination between two discrete labels. Similarly, two or more detectable labels may be selected having distinct detection means, such as a first detectable label that is a fluorophore and a second (and optionally third, fourth, etc.) detectable label that may be selected from a visible-light chromophore, a radiolabel, and/or any other type of detectable label as known in the art or provided herein. Thus, according to these and related embodiments, the compositions and methods of the present invention provide, in pertinent part, a nucleic acid cluster having an identifiable center, wherein the center region in the cluster can be distinguished from the surrounding region in the cluster.

Various embodiments of the present invention also contemplate, in part, methods for determining the nucleotide sequence(s) of one or more nucleic acid clusters that each have a detectable center label, wherein each detectable center label is detectably distinct, i.e., distinguishable, from any detectably labeled sequencing nucleotides that may be used in a sequencing reaction. In certain other embodiments, however, sequencing methods are contemplated in which a nucleic acid cluster to be sequenced may comprise a detectable center label that is not detectably distinct, i.e., that may be indistinguishable from any detectably labeled sequencing nucleotides that are used in a sequencing reaction to determine the nucleic acid sequence.

Oligonucleotide Primers

An oligonucleotide primer may be a nucleic acid molecule as provided herein that includes a sequence of contiguous nucleotides that is capable of hybridizing to a complementary polynucleotide sequence and initiating a polynucleotide polymerase reaction, including, but not limited to a primer extension, a thermal polymerase chain reaction, an isothermal polymerase chain reaction, or certain other polymerase-catalyzed extension and/or amplification reactions. Oligonucleotide primers may be about 5, about 10, about 15, about 16, about 18, about 20, about 22, about 24, or about 25 nucleotides in length, in certain embodiments. In other embodiments, oligonucleotide primers may be between about 5 and about 100 nucleotides in length, between about 10 and about 50 nucleotides in length, between about 15 and about 30 nucleotides in length, or between about 18 and about 25 nucleotides in length, or any intervening range lengths thereof. Naturally occurring or non-naturally occurring nucleotides may be present in an oligonucleotide primer as contemplated herein. In certain embodiments, the oligonucleotide primers of the invention may comprise one or more detectable labels.

Certain preferred embodiments of the present invention contemplate oligonucleotide primers that are attached at their 5' ends (or 5' termini) to a solid support. As used herein, the terms "colony primer" and "cluster primer" are used interchangeably and refer to a primer that is attached at its 5' end to a solid support, to provide an immobilized oligonucleotide primer. The immobilized primer may serve as an extension and/or amplification primer for the generation of an immobilized nucleic acid complement of a nucleic acid template, and/or for the generation of one or a plurality of immobilized copies of the nucleic acid template and/or of the immobilized nucleic acid complement. A plurality of one or two different colony primers may be used to generate nucleic acid colonies in certain embodiments of the present invention.

In one non-limiting example, a plurality of nucleic acid templates that comprise the nucleic acid sequences to be amplified, wherein the nucleic acid templates contain at their 5' ends an oligonucleotide sequence Y and at their 3' ends an oligonucleotide sequence Z, are contacted with a plurality of colony primers X, which can hybridize to the oligonucleotide sequence Z and carry at the 5' end a means for attaching the oligonucleotide primers to a solid support. In such instances sequences Y and Z can function as universal sequences that are common to all members of the plurality of templates, and X can be a universal sequence which is capable of hybridizing to all members of the plurality of templates.

In another non-limiting example, a plurality of oligonucleotide primers comprising a first and a second immobilized oligonucleotide primer X are contacted with the plurality of nucleic acid templates. Preferably, oligonucleotide sequence Z can hybridize to the first immobilized oligonucleotide primer X and the oligonucleotide sequence Y includes a sequence that is the same as the second immobilized oligonucleotide primer. The amplification can be carried out with a single immobilized primer in embodiments wherein sequences Z and Y are complementary (i.e., the ends of the templates are self-complementary).

Hybridization

Hybridization refers to the base pairing of a nucleic acid to its complement. The nucleic acid hybrids may be deoxyribonucleic acid (e.g., DNA duplexes), ribonucleic acid (e.g., RNA duplexes), or a combination thereof (e.g., DNA/RNA heteroduplexes). The specificity of single stranded DNA to hybridize complementary fragments is determined by the "stringency" of the reaction conditions. Hybridization stringency increases as the propensity to form duplexes/heteroduplexes decreases.

One or more oligonucleotide primers (e.g., colony primers) may hybridize to the 3' end of a target nucleic acid template or a complementary nucleic acid thereof (e.g., a central nucleic acid complement). In certain embodiments, the oligonucleotide primer may be 90%, 95%, 99% or 100% complementary to (e.g., identical to the complement of) the target nucleic acid. In one embodiment, the oligonucleotide primer may be 100% complementary (i.e., completely complementary or primer-specific) to the target nucleic acid sequence. In nucleic acid amplification and sequencing reactions, high stringency conditions are generally employed to favor specific primer/target hybridizations, which can be used to specifically amplify or extend target nucleic acid sequences comprising the primer-specific binding sites.

It is well understood that the stability of nucleic acid duplexes is influenced by: (1) the number of complementary nucleotide base pairs, (2) the type of base pairs, (3) salt concentration (ionic strength) of the reaction mixture, (4) the temperature of the reaction, and (5) the presence of certain organic solvents, such as formamide which decreases nucleic acid duplex stability. In general, the longer the oligonucleotide, the higher the temperature required for proper hybridization. A common approach is to vary the temperature: higher relative temperatures result in more stringent reaction conditions. (Ausubel et al., 1987) provide an excellent explanation of stringency of hybridization reactions.

To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the oligonucleotides complementary to the target sequence hybridize to the target sequence at equilibrium. Since the target sequences are generally present at excess, at Tm, 50% of the oligonucleotides are occupied at equilibrium.

Universal Primers

According to certain embodiments of the compositions and methods that are described herein, universal primers are used to generate, amplify, sequence and/or otherwise analyze nucleic acid templates and their complements. The skilled person will recognize that universal primers can amplify variable template nucleic acid sequences (e.g., "target" nucleic acids) that are flanked at their 5' and 3' ends by a common or universal sequence. A universal sequence is a region of nucleotide sequence that is common to, i.e., shared by, two or more nucleic acid molecules, where the two or more nucleic acid molecules also have regions of sequence differences. A universal sequence that may be present in different members of a collection of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize specifically to such a universal sequence. The target nucleic acid sequence-bearing molecules may be modified to attach universal adapters (e.g., non-target nucleic acid sequences) to one or both ends of the different target sequences, the adapters providing sites for hybridization of universal primers. This approach has the advantage that it is not necessary to design a specific pair of primers for each template to be generated, amplified, sequenced, and/or otherwise analyzed; a single pair of primers can be used for amplification of different templates provided that each template is modified by addition of the same universal primer-binding sequences to its 5' and 3' ends.

Solid Support

A solid support for use in a number of embodiments that are described herein refers to any solid surface or collection of solid surfaces to which nucleic acids can be covalently attached, for example, latex beads, dextran beads, polystyrene, polypropylene, polyacrylamide gel, gold surfaces, glass surfaces, optical fibers, and silicon wafers, or other materials that are typically solids at ambient room temperatures and that are amenable to chemical modification to afford covalent linkage to a nucleic acid. In one embodiment, the preferred solid support is a glass surface.

The solid support may comprise a surface that may be contained in a flow chamber such as a flow cell, allowing convenient movement of liquids across the surface to enable the transfer of reagents. Exemplary flow cells that can be used in this manner are described in WO 2007/123744, which is incorporated herein by reference in its entirety.

Nucleic Acid Immobilization on Solid Supports

According to certain embodiments contemplated herein, there are provided nucleic acids that are immobilized to a solid support. For example, colony primers, template nucleic acids, and/or nucleic acid complements (e.g., a complement of a nucleic acid template) may be attached and thereby immobilized to a solid support as described herein. Any of a wide variety of chemical or non-chemical attachment methods may be employed, including, for example, labels that are capable of binding to a ligand or receptor, or chemically-modifiable functional groups that can mediate covalent linkage of a nucleic acid to the solid support, such as the chemically-modifiable functional groups described herein. Immobilization refers to the attachment of nucleic acid to a solid support by one or more of a covalent attachment, irreversible passive adsorption, and specific high-affinity binding interactions between molecules (for example, immobilization of biotinylated molecules on an avidin-coated surface). The attachment is typically of sufficient strength that it cannot be removed by washing with water or aqueous buffer under DNA-denaturing conditions. Specific binding interactions typically refers to conditions where two binding partners remain in physical association with one another as a consequence of one or more molecular properties selected from molecular shape complementarity, electrostatic or charge attractions, hydrophobic attractions, steric interactions, hydrophilic interactions, van der Waals forces, hydrogen bonding, and the like, while structurally unrelated molecules that fail, qualitatively or quantitatively, to share such properties are unable to remain in association with either binding partner.

Nucleic acids such as oligonucleotide primers may be immobilized to a solid support by single point covalent attachment to the surface of the solid support. The point of attachment can, for example, be situated at or near the 5' end of the nucleic acid. Any suitable covalent attachment means known in the art may be used for this purpose. The chosen attachment chemistry will depend on the nature of the solid support, and on any derivatization or functionalization applied to it. An oligonucleotide primer to be immobilized may itself include a chemical moiety, which may be a non-nucleotide chemical modification, to facilitate attachment. For example, the oligonucleotide primer may include a sulphur-containing nucleophile, such as phosphorothioate or thiophosphate, located at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl)acrylamide (BRAPA), as described in U.S. patent application Ser. No. 10/585,373 and WO 05/065814, each of which is herein incorporated by reference in its entirety. Other means for attaching a nucleic acid such as an oligonucleotide primer or a template to a solid support include chemically-modifiable functional groups that can mediate covalent linkage of a nucleic acid to the solid support, such as the chemically-modifiable functional groups described herein. Attachment can also occur via ligand-receptor interactions such as those described elsewhere herein.

Chemically-Modifiable Functional Group

Chemically modifiable functional groups to be added at the 5' end of the nucleic acids to be immobilized on solid supports may be thiol, hydroxyl, dimethoxytrityl (DMT), amino, or phosphate groups, as well as carboxylic or aldehyde moieties. Examples of crosslinking agents useful to derivatize a solid support are 1-ethyl-3-(3-dimethylaminopropyl)-carbodiimide hydrochloride (EDC), succinic anhydride, phenyldi-isothiocyanate or maleic anhydride, or a hetero-bifunctional crosslinker such as, for example, m-maleimidobenzoyl-N-hydroxysuccinimide ester (MBS), N-succinimidyl[4-iodoacethyl]aminobenzoate (SIAB), Succinimidyl 4-[N-maleimidomethyl]cyclohexane-1-carboxylate (SMCC), N-y-maleimidobutyryloxy-succinimide ester (GMBS), Succinimidyl-4-[p-malei-midophenyl]butyrate (SMPB) and the sulfo (water-soluble) corresponding compounds. In a preferred embodiment, the nucleic acid templates and primers are modified with thiol, phosphate or amino group at the 5' end modification and immobilized using an immobilization solution containing 1-ethyl-3-(3-dimethylaminopropyl)-carbodiimide hydrochloride (EDC) as crosslinking agent.

In other embodiments, the chemically-modifiable functional group as described herein may refer to a chemical group such as, for example, a phosphate group, a carboxylic or aldehyde moiety, a thiol, or an amino group.

Preparation of Nucleic Acid Clusters

Methods of generating nucleic acid clusters for use in high-throughput nucleic acid technologies have been described, as noted above; see, for example, U.S. Pat. No. 7,115,400, U.S. Patent Application Publication Nos. 2005/0100900 and 2005/0059048, and PCT Publication Nos. WO 98/44151, WO 00/18957, WO 02/46456, WO 06/064199, and WO 07/010,251, each of which is incorporated by reference herein in its entirety.

As also noted above, however, currently available nucleic acid cluster technologies typically involve the generation of randomly and irregularly spaced nucleic acid clusters on a solid support. The failure of the current technologies to resolve overlapping signals from two or more nucleic acid clusters has led to less dense and lower throughput assays, in order to avoid the difficulties associated with interpreting and resolving the overlapping signals created by abutting, tightly proximate and/or extremely densely arrayed clusters. In contrast, the compositions and methods of the presently described invention embodiments provide, in pertinent part, nucleic acid clusters in which the center or origin of the nucleic acid cluster can be distinguished from the surrounding nucleic acids in the cluster, thus affording certain related advantages as described herein.

Without wishing to be bound by any particular theory, it is presently contemplated that by detectably labeling, with a detectable center label as described herein, the first strand or stands (i.e., the original template nucleic acid and/or the complement thereof) of a nucleic acid cluster that is amplified outwardly and radially from a fixed position on the solid support that is occupied by the original template and/or its complement, the origin or center of the nucleic acid cluster can be identified. As the center (origin) of the nucleic acid cluster can be identified by virtue of the signal emanating from the detectable label, the positions of two or more overlapping clusters (e.g., abutting, tightly proximate and/or extremely densely arrayed clusters that generate overlapping signals, such as the signals from fluorescent sequencing labels that otherwise could not be readily assigned to a single source cluster) can then be resolved. The signal from the labeled origin (e.g., center, or the substantially central location) of each cluster will appear as a discrete, diffraction limited spot, and hence will be focused and geometrically much smaller than a signal generated from a nucleic acid cluster that has been labeled across the entire cluster, which can't reach the diffraction limit. Unlike previously described nucleic acid clusters, in which incorporation of detectable labels at locations other than just the centers (origins) can result in ambiguity as to the source of a given signal when two or more clusters overlap on the solid support (e.g., abutting, tightly proximate and/or extremely densely arrayed clusters that generate overlapping signals that cannot be assigned to a single discrete source cluster), in the present invention embodiments, the detectable center label signals from the identifiable centers of the overlapping clusters will not overlap. Such non-overlapping detectable center label signals, even from otherwise overlapping clusters, may therefore be assigned to a single discrete source cluster with high precision.

Accordingly, in particular embodiments the present invention contemplates methods to identify and resolve overlapping signals generated from a plurality of nucleic acid clusters on a solid support, such as abutting, tightly proximate and/or extremely densely arrayed clusters. In related embodiments, detectable signals that permit unambiguous identification of the substantially central location in one or more nucleic acid clusters can be used in concert with, e.g., sequencing methods that might otherwise result in ambiguity as to the source of a given sequencing label signal (i.e., a signal that is differentiable from the center/origin signal that permits identification of the identifiable center of each cluster as provided herein) when signals from two or more clusters overlap on the solid support, or as another example, when the signals from two or more clusters overlap in an image of the solid support that has been generated using signals from sequencing labels. These and similar embodiments may be amenable to a number of high-throughput assay formats, e.g., nucleic acid sequencing, gene expression analysis, epigenetic analysis, genotyping, and others as described herein.

Signals produced by the detectable label at the center (origin) of a nucleic acid cluster, and detectable sequencing label signals (i.e., a signal that is differentiable from the center/origin signal that permits identification of the identifiable center of each cluster as provided herein, for example and without limitation, as a function of intensity, conductivity, wavelength or other spectral or physicochemical properties) may be detected using any suitable apparatus that includes an appropriate detection device, which will be apparent to the skilled artisan as a function of the assay configuration, including instrumentation, and of the particular detectable center label that is employed, and of the particular sequencing label signal (i.e., a signal that is differentiable from the center/origin signal that permits identification of the identifiable center of each cluster), such as a labeled sequencing nucleotide. For instance, a preferred detection system for fluorescent labels is a charge-coupled device (CCD) camera, which can optionally be coupled to a magnifying device, for example a microscope. Using such technology it is possible to simultaneously monitor many colonies in parallel. A confocal scanner (e.g., laser-scanning confocal microscopy) can also be used to detect signals. A label that is used to identify a central location of a cluster may be retained throughout a sequencing process, or may be removed before sequencing commences. In cases where the label is removed prior to sequencing, it can be advantageous to use a label that is the same as or similar to one or more of the labels used in the sequencing steps.

Immobilized nucleic acid clusters may be designated as indistinct or overlapping when the amplification and/or sequencing and/or other non-center label signals detected from each cluster (i.e., a signal that is differentiable from the center/origin signal that permits identification of the identifiable center of each cluster as disclosed herein) share about 0.5%, about 1%, about 2.5%, about 5%, about 10%, about 15%, about 20%, about 25%, about 30%, about 35%, about 40%, about 45%, about 50%, about 75%, about 90%, about 95%, or about 99% of the same area, for example on a solid support. Another measure is the percentage of the perimeter of a first cluster that is in apparent contact with an abutting cluster, and which can be, for example, at least about 0.5%, about 1%, about 2.5%, about 5%, about 10%, about 15%, about 20%, about 25%, about 30%, about 35%, about 40%, about 45%, about 50%, about 75%, about 90%, about 95%, or about 99% of the perimeter of the first cluster. In another embodiment, the positions of labeled sequencing nucleotides that comprise non-center labels which are incorporated into a nucleic acid molecule as provided herein during a sequencing reaction overlap if the signals detected from each labeled sequencing nucleotide (e.g., a sequencing label signal such as a signal that is differentiable from the center/origin signal that permits identification of the identifiable center of each cluster, such as a labeled sequencing nucleotide) share about 0.5%, about 1%, about 2.5%, about 5%, about 10%, about 15%, about 20%, about 25%, about 30%, about 35%, about 40%, about 45%, about 50%, about 75%, about 90%, about 95%, or about 99% of the same area.

It will be appreciated that while the shared area can be the actual physical area on a solid support, shared area may additionally or alternatively comprise the area shared in a graphical representation of the signal detected from each of the detectably labeled clusters or sequencing nucleotides, such as a representation produced by any commonly used image analysis software. Thus, the apparent overlap can be a function of the resolution of the detection system that is used to image adjacent, abutting or overlapping clusters.

Embodiments disclosed herein provide methods for producing at least one nucleic acid cluster having an identifiable center. In particular embodiments, at least 0.5, at least 1, at least 2, at least 5, at least 10, at least 25, at least 50, at least 100, at least 500, at least 1000, at least 10,000 at least 100,000, at least 1,000,000, or at least 10,000,000 or more nucleic acid clusters per square millimeter are generated on a solid support. In other various embodiments, compositions are provided that comprise one or more nucleic acid clusters each having an identifiable center.

Nucleic acid clusters can be generated from a single nucleic acid template as provided herein. In one embodiment, a single nucleic acid template may be immobilized at it 5' end to a solid support. In another embodiment, a single nucleic acid template may be immobilized through base-pairing or hybridization to an oligonucleotide primer that is immobilized, for example, at its 5' end to a solid support. The present methods contemplate the simultaneous production of one or a plurality of nucleic acid clusters, each of which may contain different nucleic acid templates. As used herein, the term "plurality" means more than one. "A plurality of copies" of nucleic acids, or "a plurality of nucleic acid clusters", refers to at least or more than 2, 3, 4, 5, 6, 7, 8, 9, 10, 20, 30, 40, 50, 60, 70, 80, 100, 500, 1000, 10,000, 100,000, 1,000,000, or 10,000,000 copies or nucleic acid clusters. The skilled artisan will appreciate that any intervening number of copies or clusters is also contemplated.

According to certain embodiments, a plurality of nucleic acid templates may comprise the nucleic acids to be amplified (e.g., target nucleic acids), wherein the nucleic acids contain at their 5' ends an oligonucleotide sequence Y and at the 3' end an oligonucleotide sequence Z. In addition, the nucleic acid (s) carry at the 5' end a functional group, as described herein and as known in the art, which allows the nucleic acid(s) to be immobilized on a solid support. In certain embodiments, a plurality of colony primers X, which can hybridize to the oligonucleotide sequence Z, carries at the primer 5' ends a functional group that allows the primers X to be immobilized to a solid support. In a preferred embodiment, there is provided a mixture comprising a plurality of nucleic acid templates and colony primers that are covalently bound to a solid support at their 5' ends. In a distinct but related embodiment, a mixture is provided comprising a plurality of nucleic acid templates that are immobilized by hybridization to immobilized colony primers, which are covalently bound to a solid support at their 5' ends. In another embodiment, pluralities of two different colony primers X may be mixed with a plurality of nucleic acid templates.

Preferably, the sequences of the colony primers X are such that the oligonucleotide sequence Z can hybridize to one of the colony primers X and the oligonucleotide sequence Y is the same as another one of the colony primers. In another embodiment, the oligonucleotide sequence Z may be complementary to oligonucleotide sequence Y, (Y'), and all of the primers X have the same sequence as oligonucleotide sequence Y. In another embodiment, the plurality of colony primers X may comprise a degenerate primer sequence and the plurality of nucleic acid templates comprise the nucleic acids to be amplified and do not contain oligonucleotide sequences Y or Z at the 5' and 3' ends respectively.

In certain embodiments, an oligonucleotide sequence Z is complementary to an oligonucleotide sequence Y and an immobilized oligonucleotide primer X comprises a sequence that is substantially identical to oligonucleotide sequence Y. In certain other embodiments, the solid support comprises a first and a second immobilized oligonucleotide primer X which are different from each other, wherein the oligonucleotide sequence Z can hybridize to the first immobilized oligonucleotide primer X and the second immobilized oligonucleotide primer X has a sequence that is substantially identical to oligonucleotide sequence Y. One of skill in the art will appreciate that the nucleic acid sequences of oligonucleotide sequences Y and Z, and of one or more colony primers X, are designed such that they hybridize specifically to their complementary sequences and display negligible binding to non-specific sequences.

In view of the present disclosure the skilled person will appreciate that in related embodiments there may be employed any number of different combinations of universal, specific, and/or degenerate oligonucleotide primers, to achieve a particular desired configuration for producing one or a plurality of nucleic clusters, each having an identifiable center, as provided herein.

In a preferred embodiment, the 5' ends of colony primers X of the invention are modified to carry a functional group to covalently attach the primers to the solid support. In addition, in certain embodiments, the colony primers can be designed to include additional desired sequences such as, for example, restriction endonuclease sites or other types of cleavage sites each as ribozyme cleavage sites or chemical cleavage sites. Such sites are advantageous for rendering clusters single-stranded and then allowing subsequent regeneration of the cluster for analysis of the complementary strand. Other desirable sequences include, but are not limited to, fold-back DNA sequences (which form hairpin loops or other secondary structures when rendered single-stranded), "control" DNA sequences which direct a protein/DNA interaction, such as for example a promoter DNA sequence which is recognized by a nucleic acid polymerase or an operator DNA sequence which is recognized by a DNA-binding protein.

Immobilization of a colony primer X to a support by the 5' end leaves its 3' end free from the support such that the colony primer is available for chain extension by a polymerase once hybridized to a complementary oligonucleotide sequence contained at the 3' end of the nucleic acid template.

Nucleic acid templates and colony primers that each have an immobilizing functional group at their 5' end may be mixed together in appropriate proportions so that when they are immobilized to the solid support an appropriate density of immobilized nucleic acid templates and colony primers is obtained. The proportion of colony primers in the mixture may be higher than the proportion of nucleic acid templates, or the ratio of colony primers to nucleic acid templates may be such that when the colony primers and nucleic acid templates are immobilized to the solid support, a "lawn" of colony primers is formed comprising a plurality of colony primers being located at an approximately uniform density over the whole or a defined area of the solid support, with one or a plurality of nucleic acid templates being immobilized individually at irregular intervals within the lawn of colony primers.

Nucleic acid templates may be provided in single stranded form or in double stranded form with one or both 5' ends modified so as to allow direct immobilization to the support. After completion of the attachment process, the strands may desirably be separated, for example, by heating to 94° C. or by using a suitable chemical denaturant (e.g., about 0.1 to about 0.5N NaOH), before washing the released strands away. It will be appreciated that in the case where both strands of the double stranded nucleic acid molecules have reacted with the surface and are both attached at their 5' ends, the result will be the same as in the case when only one strand is attached and one amplification or extension step has been performed. In other words, in the case where both strands of a double stranded template nucleic acid have been immobilized to a solid support, both strands are necessarily immobilized close to each other and are indistinguishable from the result of immobilizing only one strand and performing one amplification or extension step. Thus, single stranded and double stranded template nucleic acids might be used for providing template nucleic acids attached to the surface and are suitable for nucleic acid cluster generation.

In certain other embodiments, nucleic acid templates may be provided in single stranded form or in double stranded form with no modified 5' end(s); in which case, the nucleic acid templates can be indirectly immobilized to a solid support by hybridization to an immobilized colony primer. The single stranded and/or double stranded template nucleic acids may, according to various other contemplated embodiments, comprise one or more detectable labels, as described elsewhere herein. Immobilization of a detectably labeled nucleic acid template provides an identifiable center for any cluster amplified or formed therefrom. A double stranded nucleic acid template having both strands that are immobilized to a solid support may comprise one or more detectable labels, or alternatively, either one of the strands of the double stranded nucleic acid template that is immobilized to a solid support may comprise one or more detectable labels. Detectable labels can be added to template nucleic acids by any of a variety of methods set forth herein including, but not limited to, amplification using labeled primers and/or nucleic acids. The amplification can be carried out in solution or on solid phase prior to immobilizing the amplification products as templates on a solid phase surface where clusters will be formed.

The distance between the individual colony primers and/or the individual nucleic acid templates (and hence the density of the colony primers and/or nucleic acid templates) can be controlled by altering the concentration of colony primers and nucleic acid templates that are directly immobilized to the support. A preferred density of colony primers is at least 1 fmol/mm$^2$, preferably at least 10 fmol/mm$^2$, and more preferably between 30 to 60 fmol/mm$^2$. The density of nucleic acid templates for use in the method of the invention is typically 10,000/mm$^2$ to 100,000/mm$^2$. Higher densities are also achievable, for example, 100,000/mm$^2$ to 1,000,000/mm$^2$ and 1,000,000/mm$^2$ to 10,000,000/mm$^2$.

Controlling the density of nucleic acid templates and colony primers directly immobilized to the solid support allows the final density of nucleic acid clusters on the surface of the support to be controlled. This is due to the fact that according to the methods described herein, one nucleic acid cluster can result from the attachment of one nucleic acid template. The density of nucleic acid molecules within a single nucleic acid cluster can also be controlled by controlling the density of colony primers that are attached to the solid support. In embodiments wherein the nucleic acid templates are indirectly immobilized to the solid support, e.g., by hybridization to an immobilized colony primer, the concentration and duration of hybridization, as well as the number of hybridizations performed may be varied to control the density of the nucleic acid clusters generated on the solid support. Advantageously, the compositions and methods of the present embodiments provide higher densities of immobilized nucleic acids and higher-throughput analyses than could previously be practiced conveniently, by virtue of producing clusters having an identifiable center.

Thus, in a preferred embodiment, the present invention contemplates a composition comprising a solid support comprising one or more immobilized primers; and at least one template nucleic acid that is either directly immobilized at its 5' end to the solid support or indirectly immobilized to the solid support by hybridization to one of the one or more immobilized primers, wherein either or both of the primer and the template comprise a detectable label that may be used as a detectable center label as provided herein. In particular embodiments, the primer or the template that comprise a detectable label can be part of a cluster in which other nucleic acids of the cluster have the same sequence but do not have the detectable label.

Preparation of Nucleic Acid Templates

A library of nucleic acid templates may be prepared using techniques which are standard or conventional in the art. Generally these will be based on general molecular biology techniques. The nucleic acids to be used as templates can be obtained using methods well known and documented in the art. For example, by obtaining a nucleic acid from a biological sample as provided herein, such as total DNA, genomic DNA, cDNA, total RNA, mRNA, or cRNA, a library of nucleic acid templates can be prepared, for instance, by generating fragments therefrom by limited restriction enzyme digestion and/or by mechanical means (e.g., subjecting to shearing force).

Typically, the nucleic acid to be used as a template is first obtained in double stranded form. When the nucleic acid is provided in single stranded form, as mRNA for example, it may be first made into a double stranded form by means well known and documented in the art, for example, by synthesizing a cDNA using oligo-dT primers, reverse transcriptase, and DNA polymerase. The nucleic acid to be used as a template may obtained in double stranded form of appropriate length and used without further modifications as a nucleic acid template.

The nucleic acid to be used as a template may, for example, be obtained in double stranded form of appropriate length, and oligonucleotide sequences corresponding to specified oligonucleotide sequences Y and Z may be joined to each end, i.e., to both the 5' and 3' ends of the nucleic acid sequence, to form a nucleic acid template. This can be done using methods which are well known and documented in the art, for example by ligation, or by inserting the nucleic acid to be amplified into a biological vector at a site which is flanked by the appropriate oligonucleotide sequences. Alternatively, if at least part of the sequence of the nucleic acid to be amplified is known, the nucleic acid template containing oligonucleotide sequences Y and Z at the 5' and 3' ends respectively, may be generated by polymerase chain reaction (PCR) using appropriate PCR primers which include sequences specific to the nucleic acid to be amplified and the primer sequences, Y and Z. Before attaching the nucleic acid template to the solid support, it can be made into a single stranded form using methods which are well known and documented in the art, for example by heating to approximately 94° C. and quickly cooling to 0° C. on ice.

The oligonucleotide sequence contained at the 5' end of the nucleic acid may be of any sequence and any length and is denoted herein as sequence Y. Suitable lengths and sequences of oligonucleotide may be selected using methods well known and documented in the art, and as described elsewhere herein. For example the oligonucleotide sequences attached to each end of the nucleic acid to be amplified are normally relatively short nucleotide sequences of about 5, about 10, about 15, about 20, about 25, about 50, about 75, or about 100 nucleotides in length. The oligonucleotide sequence contained at the 3' end of the nucleic acid can be of any sequence and any length and for use in certain embodiments is denoted herein as sequence Z. Suitable lengths and sequences of oligonucleotide can be selected using methods well known and documented in the art, and as described elsewhere herein. For example the oligonucleotide sequences contained at each end of the nucleic acid to be amplified are normally relatively short nucleotide sequences of about 5, about 10, about 15, about 20, about 25, about 50, about 75, or about 100 nucleotides in length.

The sequence of the oligonucleotide sequence Z may be such that it can hybridize to one of the colony primers X. In a preferred embodiment, the sequence of the oligonucleotide sequence Y is such that it is substantially identical to another of the colony primers. In another preferred embodiment, the oligonucleotide sequence Z is complementary to oligonucleotide sequence Y and all of the colony primers X have a sequence substantially identical to oligonucleotide sequence Y.

When producing nucleic acid templates according to certain herein disclosed embodiments, additional desirable sequences may optionally be introduced by methods well known and documented in the art. Such additional sequences may include, for example, restriction enzyme sites, or certain nucleic acid tags in order to permit identification of amplification products of a given nucleic acid template sequence. Other examples of desirable sequences may include foldback DNA sequences (which form hairpin loops or other secondary structures when rendered single-stranded), "control" DNA sequences which direct protein/DNA interactions, such as for example a promoter DNA sequence which is recognized by a nucleic acid polymerase, or an operator DNA sequence which is recognized by a DNA-binding protein.

If there are a plurality of nucleic acid sequences to be amplified then the attachment of oligonucleotides Y and Z can be carried out in the same or different reaction. Furthermore, persons familiar with the art will appreciate that template nucleic acids may be prepared from multiple sources and analyzed simultaneously. Each sample of template nucleic acids could be prepared using different adapters or oligonucleotide sequences at the 5' and 3' ends. For example, sample 1 comprises adapters with the oligonucleotide sequences X and Y, sample 2 comprises adapters with the oligonucleotide sequences A and B, sample 3 comprises adapters with the oligonucleotide sequences D and E, and so forth. Once template nucleic acids have been prepared from samples 1-3, they can be mixed and combined with one or two colony primers X (specific to sample 1), one or two colony primers C (specific to sample 2), and one or two colony primers F (specific to sample 3).

In yet another embodiment, more than two, for example, three, four, or more than four different colony primers may be immobilized to the solid support, for instance, using any of the nucleic acid immobilization strategies described herein or known to the art. In this manner more than one library of nucleic acid templates, prepared from different patients, for example, and with common sequences (e.g., universal primer binding sites) that differ between the libraries (wherein common sequences attached thereto are specific for each library), can be analyzed using the methods of the present invention.

Particularly useful methods for preparing nucleic acid templates are described, for example, in Bentley et al., *Nature* 456:49-51 (2008) and US 2007/0128624, each of which is incorporated herein by reference. In particular embodiments, methods of preparing nucleic acid templates, such as those set forth above or elsewhere herein, can be carried out using labeled primers and/or labeled nucleotides in order to produce templates having labels useful for producing an identifiable center for a cluster.

In one embodiment, 1, 2, 3, 4, 5, 6, 7, 8, 9, 10 or more samples of template nucleic acids from the same, similar, or different sources may be analyzed simultaneously using the compositions and methods of the present invention.

In particular embodiments, a nucleic acid template that has been prepared can be amplified before further use in certain presently disclosed methods. Such amplification may be carried out using methods well known and documented in the art, for example by inserting the template nucleic acid into an expression vector and amplifying it in a suitable biological host, or amplifying it by PCR. This a priori amplification step is not, however essential, as certain of the methods described herein, e.g., for producing or annotating nucleic acid clusters having identifiable centers, comprise amplification steps by which multiple copies of the nucleic acid template may be produced in a nucleic acid cluster generated from a single copy of the nucleic acid template.

It will be appreciated that template nucleic acids as described herein may, in particular embodiments, comprise one or more detectable labels as described elsewhere herein. The detectable label(s) may be at the 5' end, 3' end, and/or at any position along the length of the template nucleic acid.

Cluster Formation: Primer Extension and Nucleic Acid Amplification

As used herein, the term "solid-phase amplification" refers to a nucleic acid amplification conducted on a solid support. In particular embodiments, amplification is geometric. Solid-phase amplification may comprise a nucleic acid amplification reaction comprising only one species of oligonucleotide primer immobilized to a solid support. Alternatively, the solid support may comprise a plurality of first and second different immobilized oligonucleotide primer species. Solid-phase amplification refers to any nucleic acid amplification reaction carried out on or in association with a solid support such that all or a portion of the amplified nucleic acids remain immobilized on the solid support as they are formed. In particular, the term encompasses solid phase amplification reactions analogous to standard solution phase primer extension or PCR except that one or both of the forward and reverse amplification primers is/are immobilized on the solid support.

Solid phase nucleic acid amplification reactions may generally comprise at least one of two different types of nucleic acid amplification, interfacial and surface (or bridge) amplification. For instance, in interfacial amplification the solid support comprises a nucleic acid template that is indirectly immobilized to the solid support by hybridization to an immobilized colony primer X as described herein, the immobilized colony primer may be extended in the course of a polymerase-catalyzed, template-directed elongation reaction (e.g., primer extension) to generate an immobilized complementary nucleic acid that remains attached to the solid support. After the extension phase, the nucleic acids (e.g., template and its complementary product) may be denatured such that the template nucleic acid is released into solution and made available for hybridization to another colony primer X. The indirectly immobilized nucleic acid may be made available in 1, 2, 3, 4, 5 or more rounds of primer extension or may be washed out of the reaction after 1, 2, 3, 4, 5 or more rounds of primer extension.

The second type of amplification, surface (or bridge) amplification, occurs when, on a solid support, an immobilized nucleic acid template or nucleic acid complement hybridizes to an immobilized colony primer X. The 3' end of the immobilized nucleic acid template or immobilized nucleic acid complement provides the template for a polymerase-catalyzed, template-directed elongation reaction (e.g., primer extension) extending from the complementary and immobilized colony primer X. The resulting double-stranded product "bridges" the two colony primers, and both strands are covalently attached to the support. In the next cycle, following denaturation that yields a pair of single strands (the immobilized template and the extended-primer product) immobilized to the solid support, both immobilized strands can serve as templates for new primer extension, thereby providing a mechanism for nucleic acid cluster formation.

"Nucleic acid amplification" includes the process of amplifying or increasing the numbers of a nucleic acid template and/or of a complement thereof that are present, by producing copies of the template and/or or its complement. The amplification process may, for example, be an exponential, geometric or linear solid phase amplification. In exponential amplification, the number of nucleic acid copies increases at an exponential rate. For example, in an ideal PCR reaction with 30 cycles, 2 copies of template DNA will yield $2^{30}$ or 1,073,741,824 copies. In linear amplification the number of nucleic acid copies increases at a linear rate. For example, in an ideal 4-hour linear amplification reaction whose copying rate is 2000 copies per minute, one molecule of template DNA will yield 480,000 copies. Geometric amplification, as another example, is spatially determined and the rate of amplification is between that of exponential and linear (Mercier and Slater. *Biophysical Journal. Volume* 89; July 2005; pp. 32-420).

Nucleic acid amplification may involve several components: a target nucleic acid molecule (e.g., the nucleic molecule to be amplified such that more copies of it are obtained), a molar excess of one or more amplification oligonucleotide primers which bind to the target nucleic acid molecule by specific hybridization, deoxyribonucleoside triphosphates (dATP, dTTP, dCTP and dGTP) and a polymerase enzyme. Various types of nucleic acid amplification contemplated by the present methods include primer extension, thermal polymerase chain reaction, and isothermal polymerase chain reaction, but the embodiments contemplated herein are not intended to be so limited and may also include other nucleic acid amplification strategies and methodologies as are known in the art to be compatible with the compositions and methods of the present disclosure.

Primer Extension

"Primer extension" includes the extension of one or more immobilized colony oligonucleotide primers X by polymerase-driven serial addition to the primer of one or more nucleotides as directed by a nucleic acid template according to nucleotide base-complementarity rules, when the primer (s) is hybridized to the nucleic acid template. In certain preferred embodiments described herein, the first nucleic acid complement of a template in a nucleic acid cluster may be generated by a primer extension reaction. Primer extension thus comprises the 5' to 3' extension of an oligonucleotide primer hybridized to a target nucleic acid. Primer extension may be performed using, but does not require, thermocycling (e.g., temperature fluctuations, usually controlled, that permit alternating periods of temperatures conducive to nucleic acid hybridization and temperatures conducive to denaturation of nucleic acid duplexes, typically in the presence of a thermostable polynucleotide polymerase) and may also be conducted at static (e.g., substantially invariant or isothermal) temperature. For example, when a DNA dependent polymerase such as Taq DNA polymerase is used for primer extension, the primer extension may be conducted at a temperature of 72° C. In another non-limiting example, primer extension may be carried out using a reverse transcriptase at a constant temperature of 42-50° C.

Thermal Polymerase Chain Reaction

A thermal PCR reaction includes one or a plurality of repeated temperature cycling steps e.g., amplification cycles characterized by alternating periods of temperatures conducive to nucleic acid hybridization and temperatures conducive to denaturation of nucleic acid duplexes, typically in the presence of a thermostable polynucleotide polymerase) that may be performed to accomplish the linear or exponential amplification of a nucleic acid. Generally thermal PCR is conducted using a plurality of nucleic acid duplexes that each comprise one or more primers annealed to complementary strands of a dsDNA template that has been denatured (melted apart to yield single strand nucleic acid, e.g., ssDNA) at high temperature (90° C. to 100° C.). Nucleic acid amplification of one or a plurality of copies of an immobilized nucleic acid template and/or of an immobilized nucleic acid complement of a template, such as at a substantially central location within a nucleic acid cluster as provided herein, may be performed using one or more oligonucleotide primers having their 5' ends immobilized to a solid support. Each amplification cycle comprises a melting, annealing, and polymerase-driven, template-directed (or complement-directed) extension step usually carried out at differing temperatures in the presence of a thermostable polynucleotide polymerase, nucleotide precursors to be incorporated by extension, and co-factors and ancillary reagents as will be familiar to those skilled in the art.

Isothermal Polymerase Chain Reaction

Isothermal polymerase chain reaction refers to PCR in which the temperature of a system remains constant: e.g., ΔT=0. This typically occurs when a reaction system is present in a reaction vessel that is in contact with an outside thermal reservoir (for example, heat baths and the like), and the processes occur slowly enough to allow the system to continually adjust to the temperature of the reservoir through heat exchange.

The term "substantially isothermal" as used herein is therefore intended to mean that the system is maintained at essentially the same temperature during the reaction. The term is also intended to capture minor deviations in temperature which might occur as the system equilibrates, for example when components which are of lower or higher temperature are added to the system. Thus, it is intended that the term includes minor deviations from the temperature initially chosen to perform the method and those in the range of deviation of commercial thermostats. More particularly, the temperature deviation will be no more than about +/−2° C., more particularly no more than about +/−1° C., yet more particularly no more than about +/−0.5° C., no more than about +/−0.25° C., no more than about +/−0.1° C. or no more than about +/−0.01° C. Isothermal amplification methods are well known in the art of solid phase nucleic acid cluster formation, for example, as described in U.S. patent application Ser. No. 11/725,597, which is herein incorporated by reference in its entirety.

The skilled artisan will appreciate that the initial primer extension product may comprise one or more detectable labels. In addition, one or more rounds of primer extension may be conducted under conditions wherein in each round one or a plurality of detectably labeled nucleotides may be incorporated into the primer extension products. An extension and/or amplification reaction may comprise subjecting the solid support having one or more attached nucleic acid templates and/or complements thereof, and colony primers, to conditions which induce primer hybridization, for example, by subjecting them to a temperature of around 65° C. Under these conditions an oligonucleotide sequence Z at the 3' end of the nucleic acid template will hybridize to the complementary immobilized colony primer X. Then, under conditions and in the presence of reagents that support primer extension, for example a temperature of around 72° C., the presence of a nucleic acid polymerase such as a DNA dependent DNA polymerase or a reverse transcriptase molecule (e.g., an RNA dependent DNA polymerase), or an RNA polymerase, plus a supply of nucleoside triphosphate molecules or other nucleotide precursors, for example modified nucleoside triphosphate molecules or nucleoside triphosphates that comprise one or more detectable labels, the colony primer will be extended by the addition of nucleotides complementary to the template nucleic acid sequence.

Examples of nucleic acid polymerases which can be used in these and related embodiments include DNA polymerase (Klenow fragment, T4 DNA polymerase), heat-stable DNA polymerases from a variety of thermostable bacteria (such as Taq, VENT, Pfu, Tth, Tfl DNA polymerases) as well as their genetically modified derivatives (TaqGold™, VENTexo, Pfu exo) and other polymerases, such as Bst polymerase. A combination of 1, 2, 3, 4, 5, or more polymerase may be used in extension and/or amplification steps as described herein to generate a nucleic acid cluster on a solid support. A combination of RNA polymerase and reverse transcriptase may also be used for amplification of a DNA colony. Preferably the nucleic acid polymerase used for colony primer extension is stable under thermocycling PCR reaction conditions, i.e., repeated cycles of heating and cooling, and is stable at the denaturation temperature used, usually approximately 94° C. Preferably, in thermocyling nucleic acid amplification reactions the DNA polymerase used is Taq DNA polymerase. In a preferred embodiment, isothermal nucleic acid amplification is used, preferably using Bst or Klenow DNA polymerases Preferably the nucleoside triphosphate molecules used are deoxyribonucleotide triphosphates, for example dATP, dTTP, dCTP, dGTP, or are ribonucleoside triphosphates for example dATP, dUTP, dCTP, dGTP. The nucleoside triphosphate molecules may be naturally or non-naturally occurring. In a preferred embodiment, the initial primer extension reaction comprises one or a plurality of detectably labeled nucleoside triphosphates or deoxyribonucleoside triphosphates.

Accordingly there is provided herein a method for producing at least one nucleic acid cluster having an identifiable center. In related embodiments, at least 2, 3, 4, 5, 6, 7, 8, 9, 10, 20, 30, 40, 50, 60, 70, 80, 100, 500, 1000, 10,000, 100,000, 1,000,000, or 10,000,000 nucleic acid clusters having identifiable centers may be produced. The foregoing numbers of clusters can be generated per $cm^2$ or per $mm^2$ depending on the particular analysis, configuration, or other parameter that may be desired.

Particularly useful methods of isothermal amplification are described, for example, in US 2008/0009420, which is incorporated herein by reference. Useful devices and methods for carrying out isothermal amplification are described, for example, in WO 08/002,502, which is incorporated herein by reference.

As described herein there is thus provided a method for producing at least one nucleic acid cluster having an identifiable center, which method comprises generating, on a solid support, at least one immobilized nucleic acid complement of at least one nucleic acid template, wherein the at least one nucleic acid template and/or the at least one nucleic acid complement comprises one or more detectable labels; and amplifying the at least one nucleic acid template and/or the at least one nucleic acid complement to obtain on the solid support at least one nucleic acid cluster, wherein each cluster comprises (a) a substantially central location comprising the at least one nucleic acid template and/or the at least one nucleic acid complement, and (b) a surrounding region comprising one or more immobilized copies of the at least one nucleic acid template and/or of the at least one nucleic acid complement, and thereby producing the at least one nucleic acid cluster having an identifiable center.

Nucleic acid clusters generated as described herein may comprise an identifiable center comprising at least one detectably labeled immobilized template nucleic acid and/or at least one detectably labeled immobilized nucleic acid complement, either or both of which may comprise a detectable center label as provided herein. The signal generated from these detectably labeled nucleic acids indicates a substantially central location or center of the cluster. The center of a cluster may be distinguished from the one or more immobilized copies of the at least one nucleic acid template and of the at least one nucleic acid complement that are present in the surrounding region, because these surrounding region copies lack the detectable label (e.g., a detectable center label) of the substantially central location of the cluster. In other embodiments, the center of a cluster may be distinguished from the one or more immobilized copies of the at least one nucleic acid template and/or the at least one nucleic acid complement that are present in the surrounding region, because these copies comprise a detectably different detectable label compared to that which is present in the substantially central location of the cluster (e.g., a detectable center label) or due to quenching or masking of any label present in the one or more immobilized copies of the at least one nucleic acid template and of the at least one nucleic acid complement that are present in the surrounding region. In other embodiments, the center of a cluster lacks a detectable label and therefore may be distinguished from the one or more immobilized copies of the at least one nucleic acid template and of the at least one nucleic acid complement in the surrounding region, because these copies comprise a detectable label.

Without wishing to be bound by any particular theory, the detectable label as provided herein, which in certain embodiments may be a detectable center label, is stable, such that the label can remain detectable throughout the process of nucleic acid cluster generation and during any subsequent analysis. In particular embodiments, antioxidants are used in the amplification mix to increase the amount of time that such a detectable label remains detectable. These antioxidants may be replenished throughout the methods of generating nucleic acid clusters described herein and during any subsequent analyses. These and related embodiments contemplate, in part, that a detectable label will remain substantially detectable for about 1 hour, about 2 hours, about 4 hours, about 6 hours, about 12 hours, about 24 hours, or about 48 or more hours, under the conditions typically employed to practice the presently disclosed methods. In addition, it would be understood by those having skill in the art that stable detectable labels are known (e.g., radiolabels, fluorescent labels) in the art, for example, as described in Principles of Fluorescence Spectroscopy, Joseph R. Lakowicz (Editor), Plenum Pub Corp, 2nd edition (July 1999) and the Sixth Edition of the Molecular Probes Handbook by Richard P. Haugland; Welch et al. (*Chem. Eur. J.* 5(3): 951-960, 1999); Zhu et al. (*Cytometry* 28:206-211, 1997); Prober et al. (*Science* 238:336-341, 1987); Connell et al. (*BioTechniques* 5(4):342-384, 1987); Ansorge et al. (*Nucl. Acids Res.* 15(11):4593-4602, 1987); and Smith et al. (*Nature* 321:674, 1986). Thus, in various embodiments, the extension/amplification steps can be repeated one or a plurality of times under conditions and for a time sufficient for the detectable label to remain detectable at the substantially central location in the at least one nucleic acid cluster.

Producing Nucleic Acid Clusters having Identifiable Centers

Certain preferred methods for producing one or more nucleic acid clusters having an identifiable center comprise generating at least one detectably labeled immobilized nucleic acid complement by primer extension as described above, using nucleosides or nucleotide precursors that comprise one or more detectable labels, which may be incorporated into the extension product. Accordingly, following primer extension, an immobilized nucleic acid complement has been generated, which comprises at least one detectable label and is complementary to the initial nucleic acid template. Without wishing to be bound by theory, the location of this labeled complementary nucleic acid is believed to identify the origin or center of the cluster as it is the first strand from which the rest of the cluster is produced. The second cycle of extension can also utilize labeled nucleotides, in which case the initial strands in both 'orientations' are labeled. Upon separating the immobilized complement and the nucleic acid template, for example, by heating or chemical denaturation, one or two immobilized nucleic acids will be present. For example, if the nucleic acid template was not immobilized at its 5' end to the solid support, then only one immobilized nucleic acid would be present after the first round of primer extension (e.g., the nucleic acid complement of the template, which complement has been generated by primer extension of an immobilized oligonucleotide primer such as a colony primer). In another example, if the nucleic acid template was immobilized at its 5' end to the solid support, then both the immobilized nucleic acid template and the immobilized nucleic acid complement would be present after the first round of primer extension. The template may include a label that is useful for identifying a central location or, alternatively, the template can lack such a label.

It will be understood by those skilled in the art that immobilized colony primers can be extended one nucleotide at a time during a primer extension reaction by stopping and then re-initiating the primer extension. Nucleotides comprising reversibly blocked 3' ends, for example, as described in U.S. Pat. No. 7,427,673, which is herein incorporated by reference in its entirety, are useful for stopping and re-initiating primer extension reactions. The step-wise incorporation of a labeled nucleotide into the immobilized primer may be repeated 1, 2, 3, 4, 5, 6, 7, 8, 9, 10 or more times. As also noted above, one or a plurality of detectably labeled nucleotides may be incorporated into an immobilized colony primer; these may include labeling one, two, three or all four (or more) nucleotides, and the inclusion of two or more different labeling moieties amongst the detectable labels that are present during the step of generating (e.g., by primer extension) is also contemplated. For instance, 1, 2, 3, 4, 5, 6, 7, 8, 9, or 10 nucleotides each comprising a detectable label may be incorporated into the immobilized nucleic acid complement. The nucleic acid sequence of an immobilized and detectably labeled nucleic acid complement may comprise about 1%, about 5%, about 10%, about 25%, about 50%, about 75%, about 90% about 95% or about 100% labeled nucleotides.

Following hybridization and extension steps, the duplexed nucleic acids can be denatured, which results in immobilized single stranded nucleic acids that are then available to initiate further rounds of amplification through further cycles of hybridization, extension and denaturation. Such further rounds of amplification will result in a nucleic acid cluster comprising a plurality of immobilized copies of the template nucleic acid and its complementary sequence.

In certain embodiments in which the template nucleic acid is immobilized on the solid support, the template nucleic acid would not be expected to be able to hybridize to immobilized colony primers that are located at a distance from the template that is beyond the total length of the template nucleic acid. Therefore, the nucleic acid cluster formed from such an immobilized template may be initially restricted to a relatively local region of the solid support, i.e., the area in which the initial template nucleic acid was immobilized. Once more copies of the template molecule and its complement have been synthesized by carrying out further rounds of amplification, i.e., further rounds of hybridization, extension and denaturation, then the boundary of the nucleic acid cluster being generated may be extended further, advancing however incrementally from the initial site.

Once nucleic acid clusters having identifiable centers have been generated on a solid support as herein described, certain further embodiments contemplate an additional step such as, for example, recording the center position in the cluster or annotating the center position of the cluster, for advantageous use as described herein. For example by way of illustration and not limitation, nucleic acid clusters comprising an identifiable center permit the interpretation of otherwise confounding data from overlapping clusters (e.g., closely spaced adjacent clusters that may be difficult for image analysis algorithms to resolve), as well as resolution of the origin of signals generated from the overlapping clusters.

In order to resolve the origin of the nucleic acid cluster, a signal emanating from the detectably labeled immobilized nucleic acid template and/or the detectably labeled nucleic acid complement of the template may be detected by an apparatus that comprises an appropriate detection device, and recorded on a computer memory using image analysis software. A preferred detection system for fluorescent labels is a charge-coupled device (CCD) camera, which can optionally be coupled to a magnifying device, for example a microscope. Using such technology it is possible to simultaneously monitor many clusters in parallel. For example, using a microscope with a CCD camera and a 10× or 20× objective it is possible to observe clusters over a surface of between 1 $mm^2$ and 4 $mm^2$, which corresponds to monitoring between 10,000 and 200,000 colonies in parallel. Moreover, this number will increase with improved optics and larger chips.

An alternative method of monitoring signals emanating from detectable labels present in the solid phase immobilized nucleic acid clusters having identifiable centers and produced as described herein is to scan the surface of the solid support that is substantially covered with clusters. For example, systems may be used in which up to 100,000,000 or more clusters are arrayed and can be simultaneously monitored by taking pictures with the CCD camera over the whole surface.

Any other devices allowing detection and preferably quantitation of the signal produced by a detectable label (e.g., a fluorescence signal) that may be present on the surface of a solid support may be used to monitor the nucleic acid clusters having identifiable centers as described herein. For example, fluorescent imagers or confocal microscopes are known and may be used for this purpose. If the detectable labels are radioactive, then a detection system capable of monitoring the appropriate radionuclide decay may be selected according to criteria with which the skilled person will be familiar.

In certain embodiments there is contemplated, in pertinent part, a composition comprising a solid support and one or more nucleic acid clusters having identifiable centers as described herein, each comprising a plurality of nucleic acids having the same sequence and being immobilized to the solid support, wherein each nucleic acid cluster comprises an identifiable center comprising a first subpopulation of the plurality of nucleic acids that is surrounded by a second subpopulation of the nucleic acids, wherein each of the nucleic acids in the first subpopulation comprises one or more detectable labels that distinguish the nucleic acids in the first subpopulation from the nucleic acids in the second population. These and other nucleic acid clusters comprising an identifiable center will find uses in nucleic acid sequence analysis, gene expression analysis, genotyping of subjects or biological samples, and the like, as also discussed elsewhere herein.

Annotating the Center of a Nucleic Acid Cluster

As also discussed above, according to certain embodiments the present invention provides the ability to resolve the signals generated (e.g., fluorescent signals) from two or more overlapping nucleic acid clusters. Nucleic acid clusters generated by the methods of the present invention comprise an identifiable center which identifies a substantially center location of the cluster. A nucleic acid cluster having an identifiable origin or center is generated by detectably labeling the initial nucleic acid template and or the initial nucleic acid complement of the nucleic acid cluster such that the detectable label emits a signal from substantially the center of the cluster. The signal generated by the identifiable center is detected as a small discrete spot and will not overlap with another identifiable center of a different cluster.

It is possible to resolve optical features separated on a surface by a distance approximately half the wavelength of the light used for detection. For example, when detecting 500 nm wavelength light, it is possible to resolve features separated by 250 nm or more. In this example, nucleic acid clusters of greater than 250 nm in size should thus be resolvable using the two known locations obtained from the central location of each cluster, and the sequencing of the whole cluster. It is possible to use different optical systems, for example higher magnifications to resolve the central locations of clusters. The size of the unlabelled region can be any size without affecting the ability to resolve clusters. One benefit of the invention, in particular embodiments, is that clusters can be made larger, which gives rise to a higher signal intensity during sequencing, enabling longer reads, but the larger clusters, which may overlap with each other, can still be resolved due to the central marker. Once the identifiable centers from two or more clusters have been identified, their center positions can be recorded or annotated in a computer memory. The positions of the signals generated from the nucleic acid clusters can then be compared to the identifiable center position. The correlation between one of the overlapping signals and a particular detectably labeled center would resolve the overlap and would result in assigning the data generated to a particular cluster. In particular embodiments, a label can be attached to nucleic acids in a central location via a cleavable linker. Once a central location has been detected, the label can be removed by cleavage of the linker. Cleavage can occur before or after a first cycle of sequencing is performed. In the latter case, the label can be attached via a linker that is the same as or similar to the linker that attaches labels used for sequencing and both types of labels can be removed simultaneously. If desired, labels may be removed by photobleaching such that they are not present during subsequent sequencing cycles.

There is also contemplated herein a method for annotating a center position of at least one nucleic acid cluster, comprising generating and amplifying a nucleic acid cluster having an identifiable center as described herein; and recording a center position in the at least one nucleic acid cluster by detecting the detectable center label and therefrom identifying the position of the substantially central location in the at least one nucleic acid cluster, and thereby annotating the center position of the at least one nucleic acid cluster. The detectably labeled center of the nucleic acid cluster can be identified by a number of techniques known in the art and described herein. In various embodiments, the detection system comprises a detection device to detect the signal emitted by the detectable label(s), and image analysis software that processes the data generated from the detection device and stores the data on a physical computer memory, such as a hard drive or removable disk drive.

Nucleic Acid Sequencing

Certain methods provided herein comprise determining the nucleotide sequence of one or a plurality of central nucleic acid complements and/or nucleic acid templates that may be present in nucleic acid clusters having identifiable centers. For example, situations may arise where two or more nucleic clusters overlap on a solid support (e.g., where signals from sequencing labels overlap such that assignment of a given signal to a single discrete source cluster may be difficult) in a manner that impairs the ability to obtain meaningful nucleic acid sequencing information from either cluster, such that any information retrieved from the overlapping clusters must be discarded. Accordingly, there are contemplated herein methods for assigning nucleotide sequence information to one of the overlapping clusters, based in pertinent part on the herein afforded ability to identify in each cluster the position of the center of the cluster, such that nucleotide sequence information obtained for a cluster can be correlated with its proper source cluster.

Sequencing can be carried out using a sequencing-by-synthesis technique, for example a technique wherein nucleotides are added successively to a free 3' hydroxyl group, typically provided by annealing of an oligonucleotide primer (e.g., a sequencing primer), resulting in synthesis of a nucleic acid chain in the 5' to 3' direction. These and other sequencing reactions may be conducted on the herein described solid supports bearing nucleic acid clusters having identifiable centers. The reactions comprise one or a plurality of sequencing steps, each step comprising determining the nucleotide incorporated into a nucleic acid chain and identifying the position of the incorporated nucleotide on the solid support. The nucleotides incorporated into the nucleic acid chain may be described as sequencing nucleotides and may comprise one or more detectable labels as provided herein, where the skilled person will recognize that selection of the particular detectable label(s) can be made such that the reporter properties of the sequencing label permits its being distinguished from any detectable center label(s) as provided herein that may be present. In related embodiments, each sequencing step of a sequencing reaction comprises detecting the incorporation and recording the position of a detectably labeled sequencing nucleotide. Detectably labeled sequencing nucleotides may comprise detectable labels, including, but not limited to haptens, radionuclides, enzymes, fluorescent, chemiluminescent, and/or chromogenic agents.

The methods described herein can be used in conjunction with a variety of sequencing techniques. In some embodiments, the process to determine the nucleotide sequence of a target nucleic acid can be an automated process.

Some embodiments include sequencing by synthesis (SBS) techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa, Inc., Hayward, Calif., now Illumina, Inc., San Diego, Calif.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a by-product of incorporation of the nucleotide, such as release of pyrophosphate; or the like.

Some embodiments include cycle sequencing which is accomplished by stepwise addition of reversible terminator nucleotides containing, for example, a cleavable or photobleachable dye label as described, for example, in U.S. Pat. No. 7,427,673, U.S. Pat. No. 7,414,116, WO 04/018497 and U.S. Pat. No. 7,057,026, the disclosures of which are incorporated herein by reference. This approach is being commercialized by Solexa (now Illumina Inc., San Diego, Calif.), and is also described in WO 91/06678 and WO 07/123,744 (filed in the United States Patent and Trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In another exemplary type of SBS, pyrosequencing techniques may be employed. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In accordance with the methods set forth herein, some or all of the nucleotide monomers that are used for sequencing need not have a terminator moiety. Rather, as is the case with pyrosequencing, several of the nucleotide monomers can be added to a primer in a template directed fashion without the need for an intermediate deblocking step. The nucleotide monomers can contain labels for detection, such as fluorescent labels, and can be used in methods and instruments similar to those commercialized by Solexa (now Illumina Inc.). Preferably in such embodiments, the labels do not substantially inhibit extension under SBS reaction conditions. However, the detection labels can be removable, for example, by cleavage or degradation. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluors can include fluor linked to the ribose moiety via a 3' ester linkage (Metzker, *Genome Res.* 15:1767-1776 (2005), which is incorporated herein by reference). Other approaches have separated the terminator chemistry from the cleavage of the fluorescence label (Ruparel et al., *Proc Natl Acad Sci U S A* 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. No. 7,427,673, and U.S. Pat. No. 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010,251, the disclosures of which are incorporated herein by reference in their entireties.

Some embodiments can utilize sequencing by ligation techniques. Such techniques utilize DNA ligase to incorporate nucleotides and identify the incorporation of such nucleotides. Example SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

An additional example of a sequencing platform that can be used in association with the methods described herein is provided by Complete Genomics Inc. (Mountain View, Calif.). Libraries of target nucleic acids can be prepared where target nucleic acid sequences are interspersed approximately every 20 bp with adaptor sequences. The target nucleic acids can be amplified using rolling circle replication, and the amplified target nucleic acids can be used to prepare an array of target nucleic acids. Methods of sequencing such arrays include sequencing by ligation, in particular, sequencing by combinatorial probe-anchor ligation (cPAL).

In some embodiments using cPAL, about 10 contiguous bases adjacent to an adaptor may be determined. A pool of probes that includes four distinct labels for each base (A, C, T, G) is used to read the positions adjacent to each adaptor. A separate pool is used to read each position. A pool of probes and an anchor specific to a particular adaptor is delivered to the target nucleic acid in the presence of ligase. The anchor hybridizes to the adaptor, and a probe hybridizes to the target nucleic acid adjacent to the adaptor. The anchor and probe are ligated to one another. The hybridization is detected and the anchor-probe complex is removed. A different anchor and pool of probes is delivered to the target nucleic acid in the presence of ligase. Preferably any apparatus and method of the present disclosure may be provided in an automated form. The present application provides a solution to current and emerging needs that scientists and the biotechnology industry are trying to address in the fields of genomics, pharmacogenomics, drug discovery, food characterization and genotyping, for example: in nucleic acid sequencing and re-sequencing, diagnostics and screening, gene expression monitoring, genetic diversity profiling, whole genome polymorphism discovery and scoring, the creation of genome slides (whole genome of a patient on a microscope slide) and whole genome sequencing.

A yet further aspect of the invention provides a kit for use in sequencing, re-sequencing, gene expression monitoring, genetic diversity profiling, diagnosis, screening, whole genome sequencing, whole genome polymorphism discovery and scoring, or any other applications involving the amplification of nucleic acids or the sequencing thereof. This kit comprises a plurality of nucleic acid clusters having identifiable centers bound to a solid support, as outlined above.

As used in this specification and the appended claims, the singular forms "a," "an" and "the" include plural references unless the content clearly dictates otherwise.

As used herein, in particular embodiments, the terms "about" or "approximately" when preceding a numerical value indicates the value plus or minus a range of 5%. In other embodiments, the terms "about" or "approximately" when preceding a numerical value indicates the value plus or minus a range of 10%. In yet other embodiments, the terms "about" or "approximately" when preceding a numerical value indicates the value plus or minus a range of 15%.

For example, in one embodiment, an oligonucleotide of approximately 20 nucleotides in length is equivalent to oligonucleotides that range from 19 to 21 nucleotides in length. In another embodiment, an oligonucleotide of approximately 20 nucleotides in length is equivalent to oligonucleotides that range from 18 to 22 nucleotides in length. In yet another embodiment, an oligonucleotide of approximately 20 nucleotides in length is equivalent to oligonucleotides that range from 17 to 23 nucleotides in length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements. As used herein, the term "each" when used in reference to a collection of items is intended to identify one or more individual items in the collection but does not necessarily refer to every item in the collection unless the content clearly dictates otherwise.

The practice of the present invention will employ, unless indicated specifically to the contrary, conventional methods of chemistry, biochemistry, organic chemistry, molecular biology, microbiology, recombinant DNA techniques, genetics, immunology, cell biology, stem cell protocols, cell culture and transgenic biology that are within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2001); Sambrook, et al., *Molecular Cloning: A Laboratory Manual* ($2^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-interscience; Glover, *DNA Cloning: A Practical Approach*, vol. I & II (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Fire et al., *RNA Interference Technology: From Basic Science to Drug Development* (Cambridge University Press, Cambridge, 2005); Schepers, *RNA Interference in Practice* (Wiley-VCH, 2005); Engelke, *RNA Interference (RNAi): The Nuts & Bolts of siRNA Technology* (DNA Press, 2003); Gott, *RNA Interference, Editing, and Modification: Methods and Protocols* (Methods in Molecular Biology; Human Press, Totowa, N.J., 2004); Sohail, *Gene Silencing by RNA Interference: Technology and Application* (CRC, 2004); Clarke and Sanseau, microRNA: *Biology, Function & Expression* (Nuts & Bolts series; DNA Press, 2006); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kurstad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine)

(Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008); Hogan et al., *Methods of Manipulating the Mouse Embyro* (2$^{nd}$ Edition, 1994); Nagy et al., *Methods of Manipulating the Mouse Embryo* (3$^{rd}$ Edition, 2002), and *The zebrafish book. A guide for the laboratory use of zebrafish* (*Danio rerio*), 4th Ed., (Univ. of Oregon Press, Eugene, Oreg., 2000).

All publications, patents and patent applications cited herein, whether supra or infra, are hereby incorporated by reference in their entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for sequencing nucleic acids, comprising
   (a) attaching a plurality of different nucleic acids to a surface;
   (b) amplifying the different nucleic acids on the surface to form a plurality of clusters on the surface, wherein clusters in the plurality of clusters abut or overlap with each other on the surface, wherein each of the clusters comprises copies of a single nucleic acid from the plurality of different nucleic acids; and
   (c) determining the sequences of the amplified copies in the clusters, wherein the sequences are determined by a method comprising:
      (i) obtaining images of overlapping signals emanating from the clusters that abut or overlap with each other on the surface, and
      (ii) processing the images to assign nucleic acid sequence information to a single cluster, wherein one or more nucleic acids in a cluster are distinguished from surrounding nucleic acids in the same cluster.

2. The method of claim 1, wherein the surface is contained in a flow cell.

3. The method of claim 1, wherein the amplifying in (b) is isothermal amplification.

4. The method of claim 1, wherein the diameter of each of the clusters is between 0.2 μm to 6 μm.

5. The method of claim 1, wherein the density of the plurality of clusters is in the range from 100,000 clusters per mm$^2$ to 10,000,000 clusters per mm$^2$.

6. The method of claim 1, wherein the density of the plurality of clusters is in the range from 1,000,000 clusters per mm$^2$ to 10,000,000 clusters per mm$^2$.

7. The method of claim 1, wherein the clusters comprise a circular shape.

8. The method of claim 1, wherein the clusters comprise a shape other than a circular shape.

9. The method of claim 1, wherein the amplifying uses only one species of oligonucleotide primers immobilized on the surface.

10. The method of claim 1, wherein the amplifying uses first and second different species of oligonucleotide primers immobilized on the surface.

11. The method of claim 1, wherein the image detects 100,000,000 or more clusters simultaneously.

12. The method of claim 1, wherein the one or more nucleic acids in the cluster that are distinguished from the surrounding nucleic acids in the same cluster comprise the identifiable center of the cluster.

13. The method of claim 1, wherein the determining of the sequences comprises determining a reference position in each of the clusters, wherein the reference position distinguishes the signals detected from the clusters that abut or overlap with each other.

14. The method of claim 13, wherein the reference position of each of the clusters is surrounded by a region of the respective cluster.

15. The method of claim 13, wherein the reference position of each of the clusters comprises the identifiable center of the cluster.

16. The method of claim 1, wherein the determining of the sequences comprises sequencing by synthesis.

17. The method of claim 1, wherein the determining of the sequences comprises sequencing by ligation.

18. The method of claim 1, wherein the determining of the sequences comprises repeated cycles of the obtaining of the images and the processing of the images.

19. The method of claim 1, wherein the signals comprise fluorescent signals.

20. The method of claim 1, wherein each of the clusters comprises at least 500 copies of a single nucleic acid from the plurality of different nucleic acids.

21. The method of claim 1, wherein a plurality of oligonucleotide primers is immobilized on the surface.

22. The method of claim 21, wherein the attaching comprises hybridizing the different nucleic acids to the oligonucleotide primers that are immobilized on the surface.

23. The method of claim 22, wherein the plurality of different nucleic acids comprise universal sequences that hybridize to the oligonucleotide primers that are immobilized on the surface.

24. The method of claim 23, wherein the universal sequences are present at the 5' ends of the different nucleic acids.

25. The method of claim 23, wherein the universal sequences are present at the 3' ends of the different nucleic acids.

26. An automated system comprising a processor and a non-transitory computer readable medium comprising instructions for
   (a) attaching a plurality of different nucleic acids to a surface;
   (b) amplifying the different nucleic acids on the surface to form a plurality of clusters on the surface, wherein clusters in the plurality of clusters abut or overlap with each other on the surface, wherein each of the clusters comprises copies of a single nucleic acid from the plurality of different nucleic acids; and
   (c) determining the sequences of the amplified copies in the clusters, wherein the sequences are determined by a method comprising
      (i) obtaining images of overlapping signals emanating from the clusters that abut or overlap with each other on the surface, and (ii) processing the image to assign nucleic acid sequence information to a single cluster, wherein one or more nucleic acids in a cluster are distinguished from surrounding nucleic acids in the same cluster.

* * * * *